(12) United States Patent
Ogawa et al.

(10) Patent No.: US 8,016,762 B2
(45) Date of Patent: Sep. 13, 2011

(54) DEVICE AND METHOD FOR OUTPUTTING BIOINFORMATION AND BIOINFORMATION REPORT

(75) Inventors: Yasuei Ogawa, Ichikawa (JP); Yoshiya Muraki, Hasuda (JP); Tomoyuki Yamamoto, Matsudo (JP)

(73) Assignee: Fukuda Denshi Co., Ltd., Tokyo (JP)

( * ) Notice: Subject to any disclaimer, the term of this patent is extended or adjusted under 35 U.S.C. 154(b) by 1525 days.

(21) Appl. No.: 11/407,349

(22) Filed: Apr. 20, 2006

(65) Prior Publication Data

US 2006/0258943 A1  Nov. 16, 2006

(30) Foreign Application Priority Data

Apr. 22, 2005 (JP) ................. 2005-125761
Jul. 27, 2005 (JP) ................. 2005-217355

(51) Int. Cl.
*A61B 5/02* (2006.01)
(52) U.S. Cl. ............ 600/485; 600/481; 600/300
(58) Field of Classification Search ........... 600/485–499
See application file for complete search history.

(56) References Cited

U.S. PATENT DOCUMENTS

| | | | |
|---|---|---|---|
| 4,807,638 A | 2/1989 | Sramek | |
| 6,196,974 B1 | 3/2001 | Miwa | |
| 6,322,516 B1 * | 11/2001 | Masuda et al. | 600/493 |
| 6,758,820 B2 * | 7/2004 | Narimatsu et al. | 600/492 |
| 7,326,180 B2 * | 2/2008 | Tanabe et al. | 600/500 |
| 7,452,332 B2 * | 11/2008 | Suzuki et al. | 600/483 |
| 7,657,306 B2 * | 2/2010 | Hirsh | 600/513 |
| 2002/0151803 A1 | 10/2002 | Kouou | |
| 2003/0083580 A1 | 5/2003 | Tampo et al. | |
| 2003/0088197 A1 | 5/2003 | Itagaki | |
| 2003/0139675 A1 * | 7/2003 | Ogura et al. | 600/492 |
| 2003/0236464 A1 | 12/2003 | Narimatsu et al. | |
| 2004/0064071 A1 | 4/2004 | Kasahara | |
| 2006/0258944 A1 * | 11/2006 | Takahashi et al. | 600/485 |

FOREIGN PATENT DOCUMENTS

| | | |
|---|---|---|
| EP | 0 714 629 A1 | 6/1996 |
| EP | 1 050 267 A1 | 11/2000 |
| EP | 1 306 049 | 5/2003 |
| EP | 1 332 716 A1 | 8/2003 |
| JP | 08-038437 A | 2/1996 |
| JP | 11-028193 A | 2/1999 |

(Continued)

OTHER PUBLICATIONS

Russian Decision on Grant dated Jun. 17, 2008 issued in Russian Application No. 2006113578/14(014755).

(Continued)

*Primary Examiner* — Charles A Marmor, III
*Assistant Examiner* — Karen E Toth
(74) *Attorney, Agent, or Firm* — Drinker Biddle & Reath LLP

(57) ABSTRACT

Blood pressure values measured in four limbs are plotted on first to fourth linear axes which extend from an origin in an upper right direction, an upper left direction, a lower left direction, and a lower right direction respectively, and a rectangle composed of vertices which are determined by the plotted blood pressure values is illustrated to present the blood pressure values. This allows a specific measured value in each site to be easily known, and the relationships between the blood pressure values in the four limbs are intuitively understood from the shape of the rectangle.

21 Claims, 19 Drawing Sheets

FOREIGN PATENT DOCUMENTS

| | | |
|---|---|---|
| JP | 11-318841 A | 11/1999 |
| JP | 2000-107146 A | 4/2000 |
| JP | 2000-316821 | 11/2000 |
| JP | 2002-306439 A | 10/2002 |
| JP | 2003-126054 A | 5/2003 |
| JP | 2003-199728 A | 7/2003 |
| JP | 2004-016746 A | 1/2004 |
| JP | 2004-081621 A | 3/2004 |
| JP | 2004-236679 A | 8/2004 |
| JP | 2006-296888 A | 11/2006 |
| RU | 2 085 114 C1 | 7/1997 |
| RU | 2137458 C1 | 9/1999 |
| RU | 21015 U1 | 12/2001 |
| WO | WO 00/14687 | 3/2000 |

OTHER PUBLICATIONS

Thaler: "The only EKG book you'll ever need" [Online], Dec. 30, 2002, Lippincott Williams and Wilkins, XP002389625, retrieved from URL:http://www.scst.org.uk/laurendocs/trainingdocs.htm> on Jul. 10, 2006.

\* cited by examiner

FIG. 2

| 1 | $= \dfrac{1}{k^2} \times \left(\ln \dfrac{Ps}{Pd}\right) \times (PWV)^2$ | $= \sqrt{\dfrac{1}{k^2} \times \left(\ln \dfrac{Ps}{Pd}\right) \times (PWV)^2}$ |
|---|---|---|
| 2 | $= k \times \dfrac{\left(\ln \dfrac{Ps}{Pd}\right) \times (PWV)^2}{(Ps - Pd)}$ | $= \sqrt{k \times \dfrac{\left(\ln \dfrac{Ps}{Pd}\right) \times (PWV)^2}{(Ps - Pd)}}$ |
| 3 | $= k \times \dfrac{(PWV)^2}{Pd}$ | $= \sqrt{k \times \dfrac{(PWV)^2}{Pd}}$ |
| 4 | $= \dfrac{1}{k^2} \times \left(\ln \dfrac{Pm}{Pd}\right) \times (PWV)^2$ | $= \sqrt{\dfrac{1}{k^2} \times \left(\ln \dfrac{Pm}{Pd}\right) \times (PWV)^2}$ |
| 5 | $= k \times \dfrac{\left(\ln \dfrac{Pm}{Pd}\right) \times (PWV)^2}{(Pm - Pd)}$ | $= \sqrt{k \times \dfrac{\left(\ln \dfrac{Pm}{Pd}\right) \times (PWV)^2}{(Pm - Pd)}}$ |

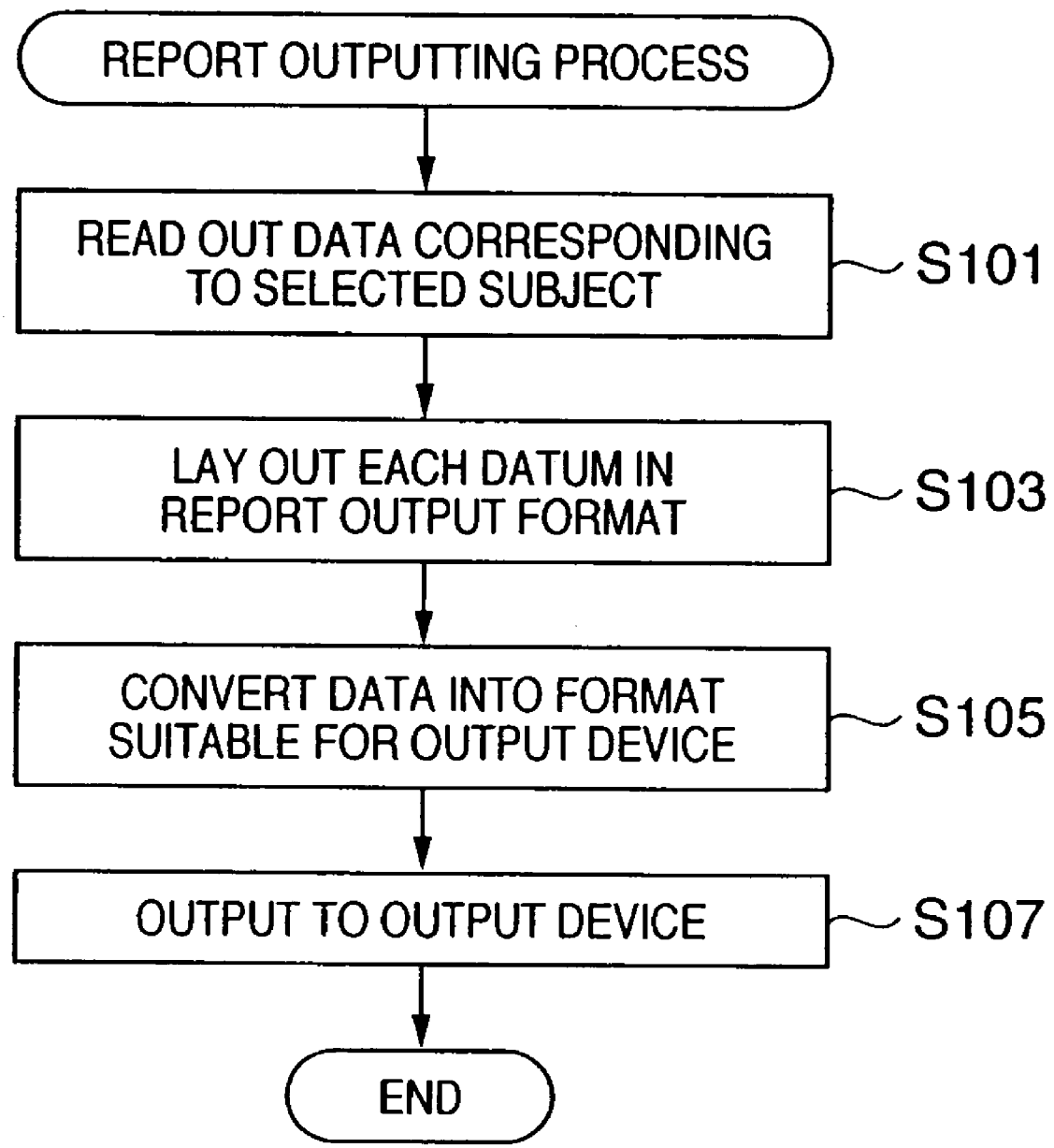

FIG. 13

| Examination Result | Date of Measurement : September 1, 2005 14:38:12 |
|---|---|

| Name : Fukuda, Ichiro | | |
|---|---|---|
| ID : 00000001 | Age : 48 | Sex : Male |

| Height : 177 cm | Weight : 60 kg |
|---|---|
| BMI : 19.1kg/m² | Heart Rate : 59 beats/minute |

| Hardness of Artery | CAVI | kCAVI | haPWV | Findings |
|---|---|---|---|---|
| Right | 7.1 | 7.2 | | Blood vessel hardness of late thirties |
| Left | 7.4 | 7.3 | | |

| Blood pressure | Right Brachum | 180/120(150) | Seriously high blood pressure |
|---|---|---|---|

| Blood Circulation of Extremities | Blood pressure barycenter (BPB) | Suspicion of hemodynamic disorder on right foot |
|---|---|---|
| | (164∞,16mmHg) | Suspicion of hemodynamic disorder on left foot |

Blood Pressure [mmHg]

Right Brachum  Left Brachum  Right Ankle  Left Ankle
180/120  160/105  130/60  125/55
(150)    (120)   (100)   (90)

ECG × 4

PCG × 4

Right arm × 1/2

Left arm × 1/2

Right foot × 1
%MAP 38
UT 126

Left foot × 1/2
%MAP 39
UT 134

| L = L1 + L2 + L3 [cm] | PEP | 100 | R-AI | 0.78 |
|---|---|---|---|---|
| 138  70  37  31 | ET | 285 | PEP/ET | 0.35 |

Second Examination Department, ... Hospital

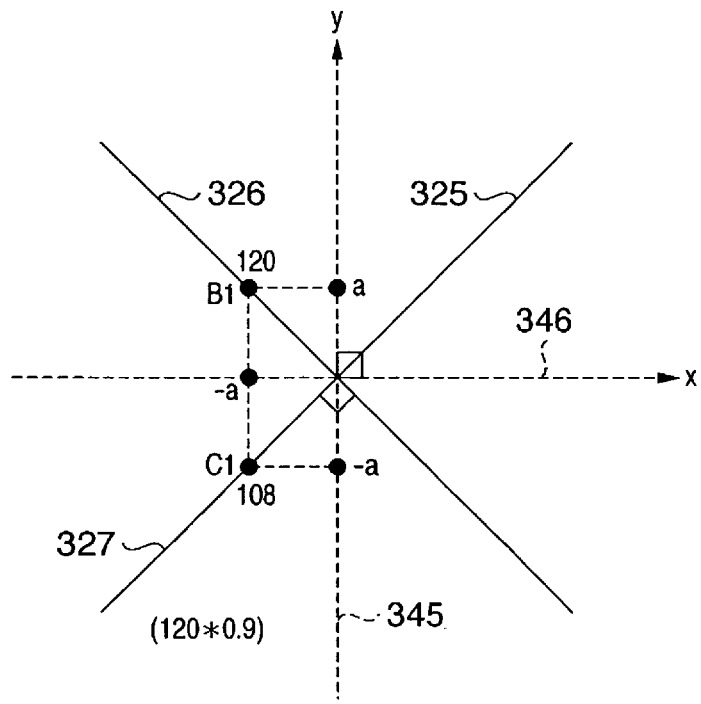
F I G. 14A
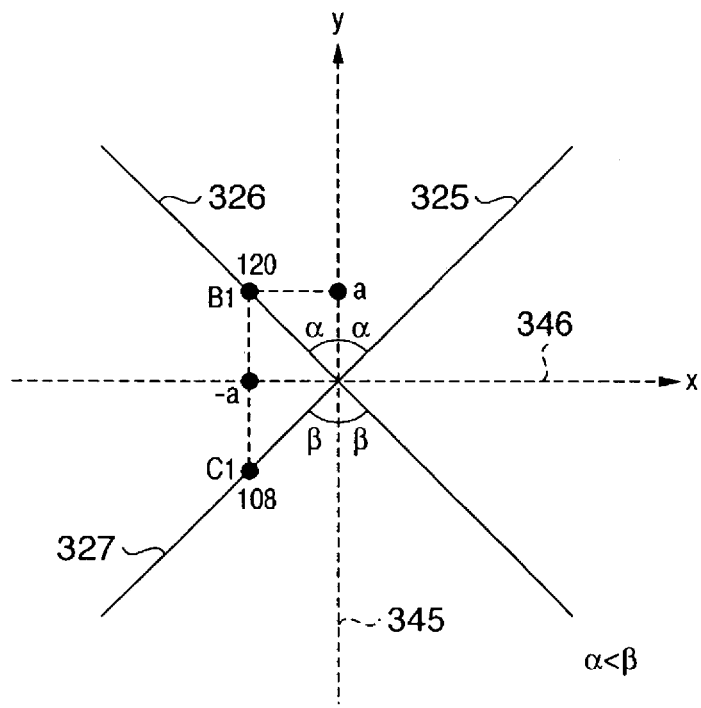
F I G. 14B

FIG. 19

| Examination Result | Date of Measurement: | | |
|---|---|---|---|
| Name: | | | |
| ID: | Age: 81 | | Sex: |
| Height: 173 cm<br>BMI: 17.3kg/m² | Weight: 52 kg<br>Heart Rate: 63 beats/minute | | |

| Hardness of Artery | Right | 10.7 | Blood vessel hardness of late thirties |
|---|---|---|---|
| Cardio Ankle Vascular Index | Left | 10.1 | |

| Artery Occlusion | Right | 1.11 | Within Normal Range |
|---|---|---|---|
| ABI | Left | 0.78 | High Possibility of Occlusion or Stenosis |

| Blood pressure | Right Brachum | 119/74(92) | Within Normal Range |
|---|---|---|---|

Blood Pressure [mmHg]

| Right Brachum | Left Brachum | Right Ankle | Left Ankle |
|---|---|---|---|
| 119/74 (92) | 122/78 (91) | 134/62 (86) | 94/55 (78) |

ECG×2

PCG×1/4

Right arm ×1

Left arm ×1

Right foot ×1
%MAP 42
U/T 166

Left foot ×1
%MAP 55
U/T 259

| L = L₁+L₂+L₃ [cm] | | | | PEP | 100 | R-AI | 0.97 |
|---|---|---|---|---|---|---|---|
| 132 | 67 | 35 | 30 | ET | 328 | PEP/ET | 0.31 |

Cardio Ankle Vascular Index
●RIGHT ●LEFT

Cardio Ankle Vascular Index
●RIGHT ●LEFT

CHANGE OVER TIME

Blood Pressure [mmHg]

20 30 40 50 60 70 80 AGE    2005/08/23    DATE

Second Examination Department, ... Hospital

DEVICE AND METHOD FOR OUTPUTTING BIOINFORMATION AND BIOINFORMATION REPORT

CLAIM OF PRIORITY

This application claims priority from Japanese Patent Application No. 2005-125761, filed on Apr. 22, 2005, and Japanese Patent Application No. 2005-217355, filed on Jul. 27, 2005, which are hereby incorporated by reference herein.

FIELD OF THE INVENTION

The present invention relates to an outputting device and method for bioinformation and particularly relates to an outputting device and method for bioinformation serving as an indicator of an arterial disease.

Further, the present invention relates to a bioinformation report for presenting at least bioinformation including blood pressures and particularly relates to a bioinformation report for readily evaluating the possibility of an arterial disease.

BACKGROUND OF THE INVENTION

Conventionally a ratio of blood pressures measured on a lower limb and an upper limb (ankle-brachial blood pressure index) has been generally used as an indicator of a vascular disease such as arteriosclerosis. As an ankle-brachial blood pressure index, for example, a ratio of systolic blood pressures measured on a brachium and an ankle (ABI) and a ratio of systolic blood pressures measured on a brachium and a toe (TBI) have been known. For example, in the case of (lower limb blood pressure/upper limb blood pressure)$\leq$0.9, the indicator is used to indicate the possibility of arteriostenosis on the lower limb.

However, when arteriosclerosis develops through the whole body, an ankle-brachial blood pressure index may present a normal value. Therefore, an ankle-brachial blood pressure index is proposed which is used as a more accurate indicator in combination with a pulse wave propagation velocity or pulse wave velocity (PWV) (for example, see Japanese Patent Laid-Open No. 2000-316821).

However, in order to discriminate an arterial disease, it is necessary to evaluate blood pressure values itself as well as a blood pressure index such as ABI. For example, when a difference in blood pressure value between right and left brachia is 20 mmHg or higher, there is a possibility of hemodynamic disorder on the brachium having a lower blood pressure. In conventional devices for evaluating ABI, the principal object is to present a ratio of blood pressure values. Measured blood pressure values have not been presented using a method for easily knowing respective measured blood pressure values or intuitively knowing the relationship with other measurement values.

SUMMARY OF THE INVENTION

The present invention is devised in view of the problem of the conventional art. An object of the present invention is to provide a bioinformation outputting device and method which can present blood pressure values used as bioinformation serving as an indicator of an arterial disease in such a manner as to allow intuitive recognition of the relationship with other measured values while facilitating recognition of specific measurement values.

That is, a gist of the present invention is a bioinformation report which presents bioinformation including at least a blood pressure value, wherein the report comprises a blood pressure value presenting region which has first to fourth linear axes extending in an upper right direction, an upper left direction, a lower left direction, and a lower right direction respectively from an origin, the first and the second axes being arranged to be symmetrical to each other relative to a straight line running straight through the origin from top to bottom of the report, and the third and the fourth axes being arranged to be symmetrical to each other relative to the straight line; a blood pressure value measured in an upper left or upper right limb is plotted on the first axis; a blood pressure value measured in an upper right or upper left limb is plotted on the second axis; a blood pressure value measured in a lower limb on the same side as that for the blood pressure value plotted on the second axis is plotted on the third axis; a blood pressure value measured in a lower limb on the same side as that for the blood pressure value plotted on the first axis is plotted on the third axis; and a rectangle composed of vertices which are determined by the blood pressure values plotted on the first to fourth axes is laid out.

Another gist of the present invention is a recording medium to print out a bioinformation report according to the present invention.

Still another gist of the present invention is a bioinformation outputting device, which comprises: obtaining means to obtain blood pressure values measured in four limbs; layout means to generate a report which presents the blood pressure values in a common two dimensional region; and outputting means to output the report, and in the report, comprising a blood pressure value presenting region which has first to fourth linear axes extending in an upper right direction, an upper left direction, a lower left direction, and a lower right direction respectively from an origin, the first and the second axes being arranged to be symmetrical to each other relative to a straight line running straight through the origin from top to bottom of the report, and the third and the fourth axes being arranged to be symmetrical to each other relative to the straight line, wherein a blood pressure value measured in an upper left or upper right limb is plotted on the first axis, a blood pressure value measured in an upper right or upper left limb is plotted on the second axis, a blood pressure value measured in a lower limb on the same side as that for the blood pressure value plotted on the second axis is plotted on the third axis, and a blood pressure value measured in a lower limb on the same side as that for the blood pressure value plotted on the first axis is plotted on the third axis, and a rectangle composed of vertices which are determined by the blood pressure values plotted on the first to fourth axes is presented.

Another gist of the present invention is a method for outputting bioinformation, which comprises: an obtaining step to obtain blood pressure values measured in four limbs; a layout step to generate a report which presents the blood pressure values in a common two dimensional region; and an outputting step to output the report, and in the report, comprising a blood pressure value presenting region which has first to fourth linear axes extending in an upper right direction, an upper left direction, a lower left direction, and a lower right direction respectively from an origin, the first and the second axes being arranged to be symmetrical to each other relative to a straight line running straight through the origin from top to bottom of the report, and the third and the fourth axes being arranged to be symmetrical to each other relative to the straight line, wherein a blood pressure value measured in an upper left or upper right limb is plotted on the first axis, a blood pressure value measured in an upper right or upper left limb is plotted on the second axis, a blood pressure value measured in a lower limb on the same side as that for the blood pressure value plotted on the second axis is plotted on the third axis, and a blood pressure value measured in a lower limb on the same side as that for the blood pressure value plotted on the first axis is plotted on the third axis, and a rectangle composed of vertices which are determined by the blood pressure values plotted on the first to fourth axes is presented.

Another gist of the present invention is a program which makes a computer operate as a device to output the bioinformation according to the present invention, or a computer readable recording medium which stores the program.

According to the present invention, blood pressure values measured in four limbs are plotted on first to fourth linear axes extending in an upper right direction, an upper left direction, a lower left direction, and a lower right direction respectively from an origin, and a rectangle composed of vertices which are determined by the blood pressure values plotted on the first to fourth axes is illustrated to present the blood pressure values, so that a specific measured value at each site is easily known, and the relationships among the blood pressure values in the four limbs are intuitively understood from the shape of the rectangle.

Other objects and advantages besides those discussed above shall be apparent to those skilled in the art from the description of a preferred embodiment of the invention which follows. In the description, reference is made to accompanying drawings, which form a part thereof, and which illustrate an example of the various embodiments of the invention. Such example, however, is not exhaustive of the various embodiments of the invention, and therefore reference is made to the claims which follow the description for determining the scope of the invention.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 2 is a diagram to show examples of formulas to calculate a blood vessel elasticity which is necessary for a bioinformation outputting device according to an embodiment.

FIG. 3 is a flowchart to explain a report outputting process with a bioinformation outputting device according to an embodiment of the present invention.

FIG. 13 is a diagram to show an example in which a bioinformation report according to an embodiment is applied to a comprehensive report which includes other measurement results.

FIGS. 14A and 14B are diagrams to explain an example of a report format output by a bioinformation outputting device according to a second embodiment.

FIG. 19 is a diagram to show an example in which the bioinformation report of FIG. 18 is applied to a comprehensive report which includes other measurement results.

DETAILED DESCRIPTION OF THE PREFERRED EMBODIMENTS

Preferred embodiments of the present invention will be specifically described below in accordance with the accompanying drawings.

First Embodiment (Device Configuration)

Figure 1:
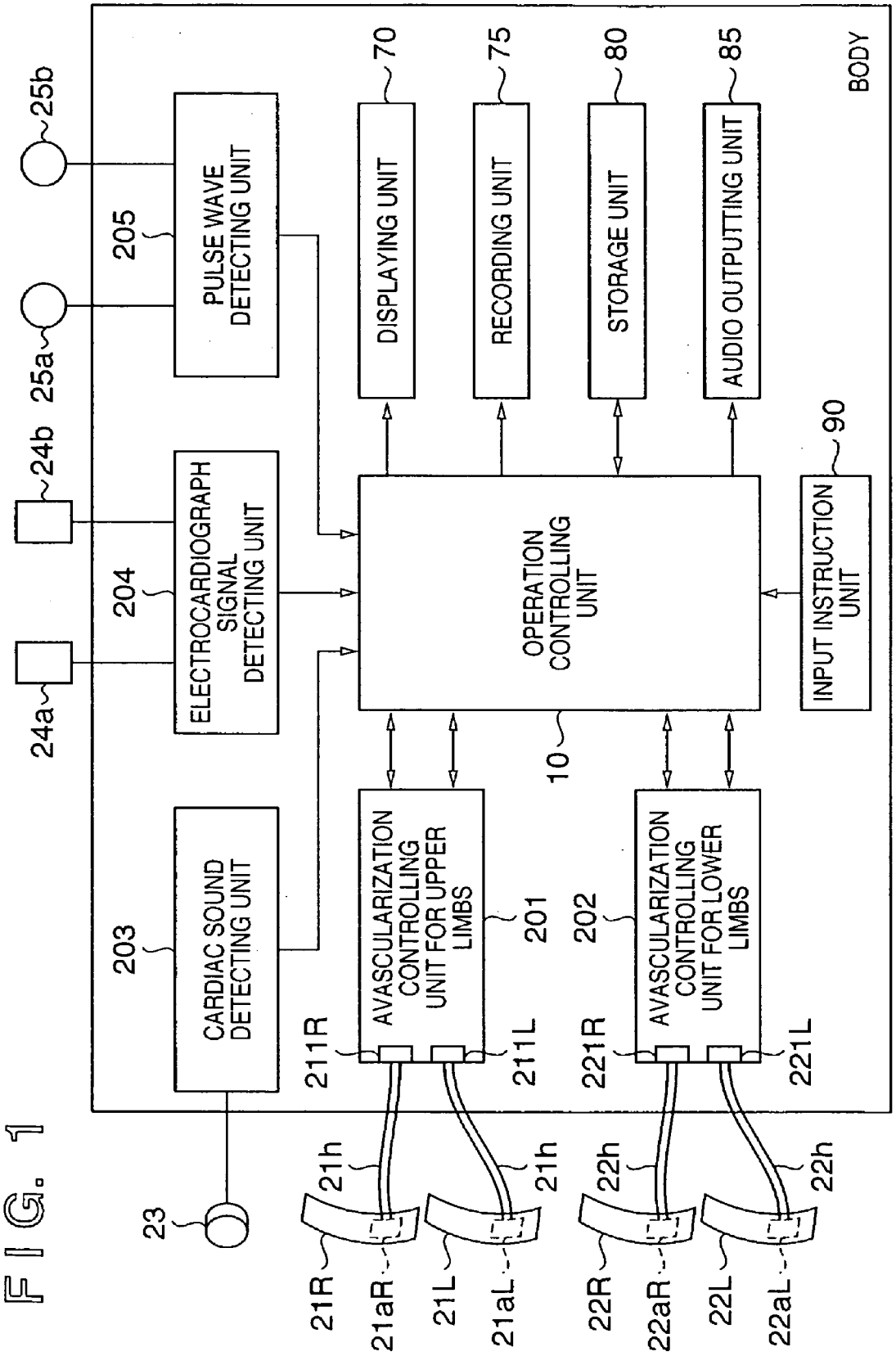
FIG. 1 is a block diagram to show an example of a configuration of a bioinformation measuring device as an example of a bioinformation outputting device according to an embodiment of the present invention.

FIG. 1 is a block diagram showing a structural example of a bioinformation measuring device which is an example of a bioinformation outputting device according to an embodiment of the present invention.

The present embodiment will describe an example in which the present invention is applied to a bioinformation measuring device capable of obtaining kinds of bioinformation. In the bioinformation outputting device of the present invention, at least measured blood pressure values in four limbs have to be obtained in some way. The measurement results may be obtained by, for example, reading data from a storage device or the like. In this case, the function of measuring blood pressure values is not necessary.

An operation controlling unit 10 controls the operations of the overall bioinformation measuring device of the present embodiment. The operation controlling unit 10 is, for example, a general-purpose computer including a CPU, ROM, RAM (including nonvolatile RAM) and various interfaces (not shown). For example, the CPU executes control programs stored in ROM and bulk memory such as an internal or external hard disk and an optical disk, so that the operations discussed below are performed and controlled. As a matter of course, all the operation are not necessarily processed by software and at least some of the operations may be implemented by hardware.

The operation controlling unit 10 controls an avascularization controlling unit 201 for upper extremity and an avascularization controlling unit 202 for lower extremity to measure a diastolic blood pressure Pd, a systolic blood pressure Ps, and a mean blood pressure Pm on an upper extremity (e.g., a brachium) and a lower extremity (e.g., an ankle or toe). ABI (the ratio of a blood pressure value on a brachium (representative) and a systolic blood pressure value on a right or left ankle) and TBI (the ratio of a blood pressure value on a brachium (representative) and a systolic blood pressure on a right or left toe) may be determined from the measurement results.

The operation controlling unit 10 can further calculate a pulse wave propagation velocity between the heart (aortic valvular opening) and an ankle, between the heart and a toe, or between sites where cuffs are attached, by using pulse wave signals supplied from the avascularization controlling unit 201 for upper extremity and the avascularization controlling unit 202 for lower extremity (a cardiac sound signal supplied from a cardiac sound detecting unit 203, an electrocardiograph signal supplied from an electrocardiograph signal detecting unit 204, and a carotid pulse, a femoral artery pulse, and a popliteal artery pulse or the like supplied from a pulse wave detecting unit 205 may be selectively used when necessary) and a blood vessel length (corresponding to a predetermined blood vessel length) between measured sites.

In response to the control of the operation controlling unit 10, the avascularization controlling unit 201 for upper extremity and the avascularization controlling unit 202 for lower extremity control the pressurization/depressurization (avascularization) of the compression bladders (21aR, 21aL, 22aR, 22aL) of cuffs 21R and 21L and 22R and 22L, which are connected via hoses 21h and 22h, by using pumps, exhaust valves, and so on (not shown). The avascularization controlling unit 201 for upper extremity and the avascularization controlling unit 202 for lower extremity comprise sensors for detecting pulse waves propagating through the hoses 21h and 22h, for example, pressure sensors (211R and L and 221R and L) are provided by which pulse waves propagating through the compression bladders and hoses are converted to electric signals and outputted to the operation controlling unit 10. In FIG. 1, the avascularization controlling unit 201 for upper extremity and the avascularization controlling unit 202 for lower extremity are separated from each other but may be provided as one unit. In the following explanation, cuffs 21 and cuffs 22 not including R or L indicate both of right and left cuffs 21 and 22.

The cardiac sound detecting unit 203 supplies, to the operation controlling unit 10, a cardiac sound signal having been detected from a subject by a cardiac sound microphone 23. The cardiac sound signal is mainly used for determining the starting point of a pulse wave in the heart.

The electrocardiograph signal detecting unit 204 obtains electrocardiograph signals detected from electrocardiograph electrodes 24a and 24b and supplies the signals to the operation controlling unit 10. The electrocardiograph signals are obtained as necessary in more comprehensive diagnosis.

The pulse wave detecting unit 205 supplies, to the operation controlling unit 10, pulse waves having been detected by the pulse wave sensors 25a and 25b, to be specific, a carotid pulse, a femoral artery pulse, and a popliteal artery pulse. Moreover, sensors similar to pulse wave sensors 25a and 25b may be disposed on sites where the cuffs 21 and 22 are attached (including sensors in the cuffs 21 and 22) and pulse waves may be detected from these pulse wave sensors.

Further, the operation controlling unit 10 is connected to a displaying unit 70 which can display/output various kinds of operation guidance, measurement results and diagnosis indicators, a recording unit 75 which is an image forming device such as a printer capable of recording and outputting measurement results and diagnosis indicators, a saving unit 80 including, for example, a hard disk drive, a writable optical disk drive, and nonvolatile semiconductor memory for storing measurement results and diagnosis indicators, an audio outputting unit 85 which can output sound of guidance and kinds of alarm sounds, and an inputting/command unit 90 which includes a keyboard, a mouse, a button, and a touch panel and enables input and instruction for the user.

Additionally, the following may be provided: a wire and/or radio communications interface for communications with other devices, and a storage device or the like using a removable medium. The displaying unit 70 and the recording unit 75 may be connected outside. In other words, in addition to the displaying unit 70 and the recording unit 75 which are included in the body of the device, an external display device with a larger display area and/or a larger number of display colors and an external recording device with a larger printing area and/or a larger number of printed colors may be connected. With this configuration, it is possible to simultaneously obtain a smaller body and a variety of outputs. In this case, a known display interface or printer interface is provided.

(Measurement: Preparation Before Measurement)

The following will describe steps and operations for measurement using the bioinformation outputting device configured thus. Measurement with the highest accuracy will be discussed below. Initialization for the operations of the device, for example, time setting has been completed.

First, for preparation, the cuffs, sensors and so on are attached to a subject. To be specific, the cuffs 21R/21L for upper extremity are attached to the right/left brachia of the subject and the cuffs 22R/22L for lower extremity are attached to the right/left ankles or toes of the subject. Although the cuffs attached to ankles and toes are different in configuration, the cuffs will be both described as cuffs 22 for lower extremity. The cuffs 21 and 22 can be attached by a hook and loop fastener or the like.

Further, the electrocardiograph electrodes 24a and 24b are attached to, for example, left and right wrists. For preferable detection, cream or the like is applied to the attachment sites as usual. The sites where the electrocardiograph electrodes are attached can be changed according to the kind of obtained lead. In the case where pulse waves are measured by a mechanism other than the cuffs, for example, separate pulse wave sensors on the sites where blood pressures are measured or around the sites, the pulse wave sensors are attached at this point of time.

The cardiac sound microphone 23 is attached with a tape to a predetermined position on the chest of the subject (II interspace sternum edge). Moreover, the pulse wave sensor 25a is attached to the carotid artery pulsation part of the neck. Moreover, the femoral artery pulse sensor 25b is attached to the groin when necessary.

Subsequently, subject's personal information including age, sex, height and weight is inputted using the inputting/command unit 90. According to a predetermined formula based on the value of the height, the corresponding blood vessel length is determined. In some cases, the blood vessel length is determined according to a predetermined formula by measuring distances between the sites where the cuffs 21 and 22 are attached and the II interspace sternum edge with a scale or the like, and inputting the distances. Preparation before measurement is completed thus.

(Measurement: Pulse Wave Measurement)

When preparation for measurement is completed and an instruction to start measurement is issued from, for example, the inputting/command unit 90, the operation controlling unit 10 first starts measuring pulse waves on sites where blood pressures are measured or around the sites. When pulse waves are measured using the cuffs, the order of measurement can be arbitrarily set. First, an instruction to start pressurization to the right brachial cuff 21R is issued to the avascularization controlling unit 201 for upper extremity.

The avascularization controlling unit 201 for upper extremity injects air into the cuff 21R to inflate the compression bladder 21aR. At this point, the pressure applied by the cuff 21R to a body surface (cuff internal pressure detected by the pressure sensor 211R) can be set low as long as a pulse wave can be detected. For example, the pressure can be lower than the typical diastolic blood pressure value.

A pulse wave propagates as a pressure wave of air from the compression bladder 21aR through the hose 21h and is detected by the pressure sensor 211R. The pulse wave is converted to an electric signal (generally a pressure sensor converts a pressure into an electric signal and outputs the signal) and outputted to the operation controlling unit 10 as a pulse wave signal obtained from the cuff 21R. The operation controlling unit 10 records the pulse wave signal in the saving unit 80. When a predetermined amount of pulse waves is measured with a sufficient amplitude, the exhaust valve is opened by the avascularization controlling unit 201 for upper extremity to evacuate the cuff 21R.

These pulse wave measurement operations are performed simultaneously or sequentially on all the cuffs and pulse waves are measured on sites where blood pressures are measured or around the sites. When pulse waves are detected by the pulse wave sensors different from those of the cuffs, pulse waves may be obtained simultaneously or sequentially from all the sensors and recorded.

(Measurement: Blood Pressure Measurement)

Subsequently the operation controlling unit 10 starts measuring blood pressures. Also in this case, the order of measurement can be arbitrarily set. First an instruction to start pressuring the right brachial cuff 21R is issued to the avascularization controlling unit 201 for upper extremity.

The avascularization controlling unit 201 for upper extremity injects air into the cuff 21R, inflates the compression bladder 21aR, and pressurizes an attachment site. A pulse wave propagates as a pressure wave of air from the compression bladder 21aR through the hose 21h in response to the pressurization, and the pulse wave is detected by the pressure sensor 211R. The pulse wave is converted to an electric signal (generally a pressure sensor converts a pressure into an electric signal and outputs the signal) and outputted to the operation controlling unit 10 as a pulse wave signal obtained from the cuff 21R.

The operation controlling unit 10 causes the avascularization controlling unit 201 for upper extremity to inject air into the compression bladder 21aR until a pulse wave detected by the pressure sensor 211R becomes too small to be detected as a waveform and the attachment site of the cuff is avascularized or until the pressure reaches a predetermined cuff pressure at which the attachment site of the cuff is sufficiently avascularized. And then, pressurization is stopped when a pulse wave becomes too small to be detected as a waveform or when the cuff pressure reaches a predetermined value. The cuff pressure (internal pressure) at this point can be detected by the pressure sensor 211R. And then, the avascularization controlling unit 201 for upper extremity is instructed to gradually reduce the cuff pressure.

The avascularization controlling unit 201 for upper extremity adjusts the exhaust valve (not shown) and starts recording detected pulse wave signals while depressurizing the cuff at a constant rate by releasing air from the compression bladder 21aR. Cuff pressures are also continuously detected by the pressure sensor 211R. The detection of pulse waves is started again in the process of depressurization, and a systolic blood pressure Ps, a mean blood pressure Pm, and a diastolic blood pressure Pd are determined by cuff pressures on a point where a pulse wave rapidly increases in amplitude, a point where a pulse wave has the maximum amplitude, and a point where a pulse wave rapidly decreases in amplitude. The cuff pressure can be calculated also by a value at the start of depressurization, a depression rate, and a decompression time. Such a method of measuring blood pressures is known as oscillometric method (volume pulse wave vibration method). When the diastolic blood pressure is determined, the cuff is depressurized without stopping.

Such a process for blood pressure measurement is similarly performed on the other cuffs 21L, 22R and 22L, and the blood pressure measurement of upper and lower limbs is completed.

The measured diastolic blood pressure value, systolic blood pressure value, and mean blood pressure value are associated with the pulse wave signals having been detected at the same site and the values are stored in the saving unit 80.

(Measurement: PWV Measurement)

With the above measurement results of blood pressures and pulse waves, a report (described later) can be generated. However, in the present embodiment, another bioinformation is measured to obtain another useful indicator for the diagnosis of an arterial disease. The following will first discuss the measurement of PWV. When carotid pulses are detected using the pulse wave sensor 25a, the operation controlling unit 10 obtains the pulse waves through the pulse wave detecting unit 205 and detects the generation of cardiac sound (e.g., II sound) corresponding to the rising edge of the pulse wave from a cardiac sound signal having been obtained through the cardiac sound detecting unit 203. The pulse waves and the cardiac sound signal undergo proper processing such as AD conversion and are stored in the saving unit 80. PWV is determined as follows:

$$PWV = AF/(t+tc)$$

where AF represents a blood vessel length to the II interspace sternum edge and the site (ankle or toe) where the cuff 22R is attached, t represents a time difference from the rising edge of a carotid pulse (or brachial pulse wave) to the rising edge of an ankle (or toe) pulse wave, and tc represents a time difference from the rising edge of the II sound of cardiac sound to the notch point of the carotid pulse (or brachial pulse wave).

When the pulse wave sensor 25a is not used, PWV (also referred to as baPWV) may be determined as follows: an estimated blood vessel length is determined by a difference between a distance from the heart (the starting point of an aorta) to the site where the cuff 21R is attached and a distance from the heart (the starting point of an aorta) to the site where the cuff 22R is attached, and the estimated length is divided by a time difference between the rising point of a pulse wave measured by the cuff 21R attached to a brachium and the rising point of a pulse wave detected by the cuff 22R. Alternatively PWV may be similarly determined by a time difference between pulse waves measured on two given points and a blood vessel length (or its reduced value) between the points of measurement.

At the completion of measurement of PWV, the operation controlling unit 10 causes the avascularization controlling unit 201 for upper extremity and the avascularization controlling unit 202 for lower extremity to release the cuffs, stores the measurement results in the saving unit 80, and completes the process of measurement.

As described above, blood pressures and pulse waves are measured on the right and left brachia and right and left ankles/toes in the present embodiment. In order to attain the effect of a report format (described later) which is a characteristic of the present embodiment, blood pressures and pulse waves are measured on at least two points of a living body. Further, PWV may be calculated between the heart and ankle and between the heart and toe, and may be calculated both on the right and left ankles or toes. Moreover, PWV may be calculated between the heart (the starting point of an aorta) and brachium, between the heart and knee, between the thigh and ankle, and between the brachium and wrist.

(Calculation of Blood Vessel Elasticity)

Subsequently the operation controlling unit 10 calculates blood vessel elasticity. The blood vessel elasticity may be values determined by, for example, Formulas 1 to 5 shown in FIG. 2 where k represents a constant. Which formula should be used is determined beforehand. As a matter of course, the blood vessel elasticity can be calculated using two or more of the formulas.

Blood pressure values (systolic blood pressure Ps, mean blood pressure Pm, and diastolic blood pressure Pd) used in Formulas 1 to 5 are ideally blood pressure values at the center points of sections where PWVs have been measured. For example, measurement values on a brachium can be used in place of the blood pressure values. The blood pressure value at the center point may be estimated based on a predetermined conversion formula and a measurement value of blood pressure at a site where pulse waves have been measured to calculate PWV. Further, PWV used for calculating the blood vessel elasticity may be any one of measurement results obtained between the heart and ankle, between the heart and toe (or between other two points).

Moreover, it is preferable to store the measured bioinformation and values such as calculated PWVs and blood vessel elasticity so as to correspond to the personal information of the subject and the date and time of measurement. For example, a folder or directory is generated for each subject, a folder or directory is further generated in the folder or directory of the subject for each time of measurement, and then obtained blood pressure values and pulse wave signals or the like are stored in the folder or directory.

As mentioned at the beginning of the present embodiment, the present embodiment described an example where the present invention is applied to the bioinformation measuring device capable of obtaining kinds of bioinformation. Hence, the measurements of other kinds of bioinformation, to be specific, the measurements of pulse waves, electrocardiograms, cardiac sounds or the like were described and the calculation of PWV and blood vessel elasticity was described in addition to the measurements of blood pressures. The minimum requirement of the bioinformation outputting device of the present invention is the function of outputting a report in the following format based on the measurement results of and blood pressure values of the four limbs.

For example, in the simplest configuration of the bioinformation outputting device capable of outputting a report in the format below, software for outputting the report discussed below is installed in a computer which is commercially available as a personal computer. In this case, the measurement results of bioinformation including blood pressures can be obtained from a removable medium or a network. Also in this case, the report may be outputted to either an internal or external display of the computer and a printer directly or indirectly connected to the computer.

(Output of Report)

Referring to the flowchart of FIG. 3, the output of a report in the bioinformation outputting device will be described below. In this case, the report is outputted by, for example, the recording unit 75 which is a color printer. As described above, the report may be outputted to an external display device or an external outputting device as well as the displaying unit 70.

The report may be automatically outputted after measurement. For example, a list of past subjects in the saving unit 80 can be displayed by the displaying unit 70 and measurement results can be outputted regarding a subject having been selected from the list by the inputting/command unit 90. In this case, measurement results are outputted regarding a subject having been selected from the list of past subjects.

First, the operation controlling unit 10 reads the personal information and measurement results of the selected subject from the saving unit 80 (step S101). Then, the read information is converted to a predetermined display format and laid out in an output format (described later) (step S103). In this step of the present embodiment, each representative pulse wave is deformed (scaled) described later, the mean blood pressure is plotted, and the measurement results of each site are laid out.

At the completion of the layout, the information is converted to a format for enabling output in the destination of output, for example, the recording unit 75 (step S105). The format conversion includes, for example, resolution conversion corresponding to the destination of output (72 or 96 dpi for display and 400 to 600 dpi for printing), color conversion (conversion to monochrome output, increase/reduction in the number of colors, and so on), scaling, and conversion to a bitmap. After the conversion to a format suitable for the destination of output, the converted data is outputted to the destination as report data (step S107) and then displayed or printed.

As long as the bioinformation outputting device can obtain previously measured data through a network or a removable storage medium or the like, even if the bioinformation outputting device does not have the function of measuring bioinformation, a report can be outputted by similar processing. In other words, the bioinformation outputting device first obtains list information on measurement data (including a list of subjects' names) and displays the information on a display. After a subject is selected using an inputting device such as a keyboard and a mouse, processing is performed as in steps S101 to S105, and the information is outputted to a predetermined destination of output, for example, a display or a printer (step S107). Thus, a similar report is displayed or printed.

(Format of Bioinformation Report)

Figure 4:
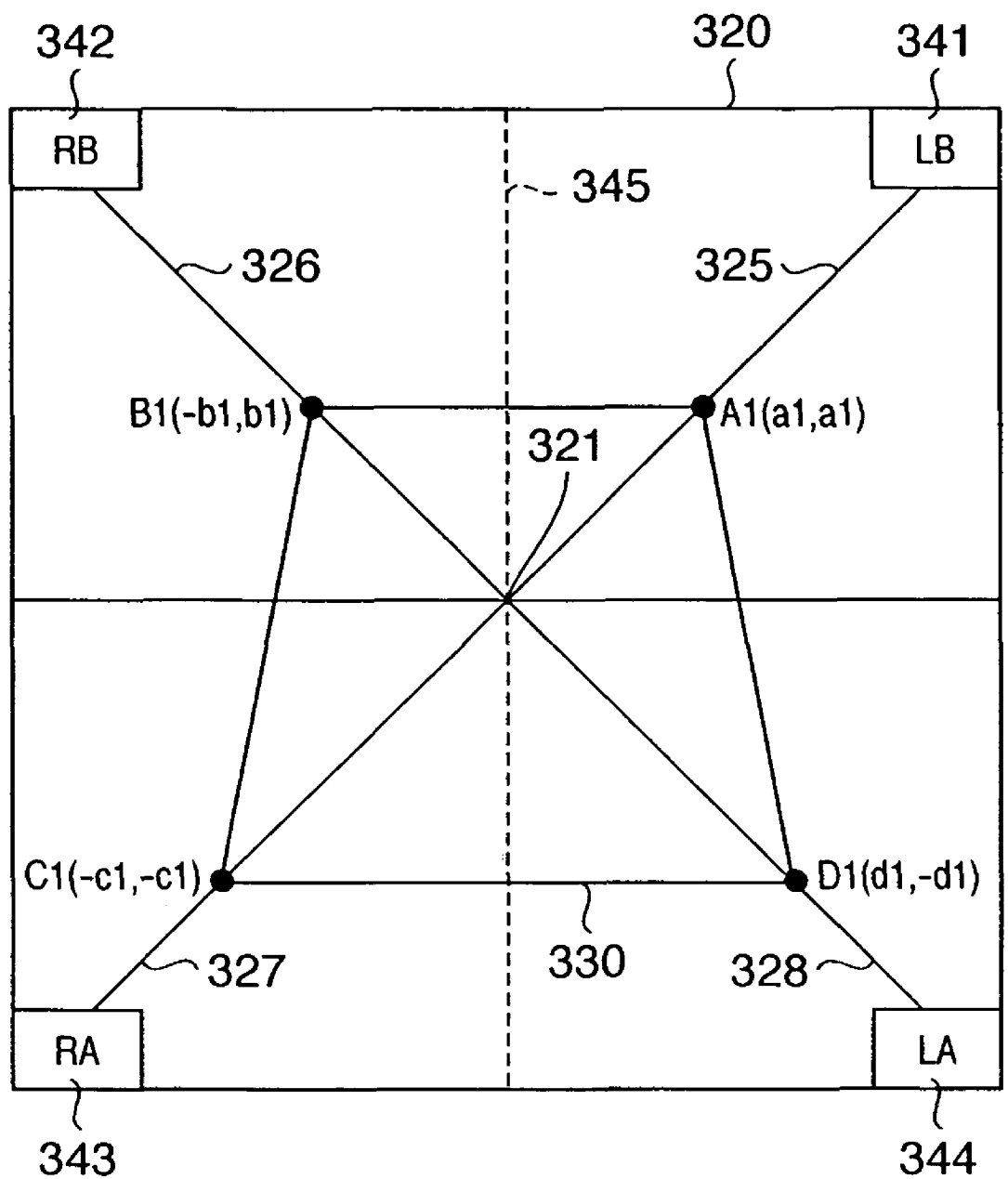
FIGS. 4 to 12 are diagrams to explain examples of a report format output by a bioinformation outputting device according to a first embodiment.

FIG. 4 shows an example of a bioinformation report outputted by the bioinformation outputting device of the present embodiment. The following will only discuss the report format of blood pressure measurement values, which is a characteristic of the present embodiment. It is needless to say that the report may include at least one or more of the other measurement values.

A report has a blood pressure value presenting region 320 which is two dimensional to present blood pressure values. A generally central point of the blood pressure value presenting region 320 is set as an origin 321, and first to fourth linear axes 325 to 328 extend in an upper right direction, an upper left direction, a lower left direction, and a lower right direction respectively from the origin 321. The first and the second axes 325 and 236 run through the origin 321, and are arranged to be symmetrical to each other relative to a straight line 345 running straight from top to bottom of the report, while similarly the third and the fourth axes are arranged to be symmetrical to the straight line 345. There is no need to illustrate the straight line 345 in the report, but the straight line 345 may be illustrated.

In the example shown in FIG. 4, the first axis 325 and the third axis 327, and the second axis 326 and the fourth axis 328 are drawn as a straight line respectively, and these two straight lines are orthogonal to each other, but what is essential is that the information can be plotted in symmetry axes at least by upper limb and lower limb.

In the report of this embodiment, the first to fourth axes 325 to 328 are plotted in correspondence with the blood pressure values measured in four limbs. Specifically, on the first axis 325 is plotted with a blood pressure value measured in an upper left or upper right limb, on the second axis 326 is plotted with a blood pressure value measured in an upper right or upper left limb, on the third axis 327 is plotted with a blood pressure value measured in a lower limb on the same side as the one for the blood pressure value plotted on the second axis 326, and on the fourth axis is plotted with a blood pressure value measured in a lower limb on the same side as the one for the blood pressure value plotted on the first axis 325.

In the example illustrated in FIG. 4, a blood pressure value A1 measured in an upper left limb (LB: Left Brachium) is plotted on the first axis 325, a blood pressure value B1 measured in an upper right limb (RB: Right Brachium) is plotted on the second axis 326, a blood pressure value C1 measured in a lower right limb (RA: Right Ankle) is plotted on the third axis 327, and a blood pressure value D1 measured in a lower left limb (LA: Left Ankle) is plotted on the fourth axis 328. The each left and right positions to plot the measured blood pressure values are interchangeable, and the blood pressure values measured in an upper right limb and an lower right limb may be plotted on the first and fourth axes, and the blood pressure values measured in an upper left limb and a lower left limb may be plotted on the second and third axes.

In FIG. 4, the A1 to D1 are expressed as coordinate values in an orthogonal coordinate system in which a common origin 321 is provided and the line 345 is specified as the y axis.

The positions to plot the values in upper limbs and lower limbs are also interchangeable, but it is unnatural to plot a blood pressure value measured in an upper limb on an axis which extends downward, unless there is a compelling reason, so the blood pressure values measured in upper limbs will be plotted on the first and the second axes 325, 326 which extend upward from the origin 321.

The upper and lower positions and the left and right positions may be interchanged to plot the blood pressure values measured in upper limbs in a plane on the right side, and plot the blood pressure values measured in lower limbs in a plane on the left side, and in this case, a blood pressure value measured in an upper right limb is plotted on the first axis, a blood pressure value measured in an upper left limb is plotted on the fourth axis, a blood pressure value measured in a lower right limb is plotted on the second axis, and a blood pressure value measured in a lower left limb is plotted on the third axis. Similarly, the blood pressure values measured in an upper limbs may be plotted in a plane on the left side, and the blood pressure values measured in a lower limbs may be plotted in a plane on the right side.

In the example illustrated in FIG. 4, the first to fourth axes 325 to 328 have common scales defining the origin as 0 (the scales themselves may or may not be illustrated). The common scales mean that the points on each axis which are at the same distance from the origin indicate the same value, and there may be some sections in which the increase (scaling rate) of value per unit distance (scale) is different from the other sections.

A report according to this embodiment has one feature to express a rectangle 330 composed of vertices which are determined by the blood pressure values plotted on each axis. The illustration of such a rectangle allows the relationships between the blood pressure values at the four limbs to be intuitively understood from its shape.

That is, the slopes of the side A1-B1 and the side C1-D1 of the rectangle 330 show a magnitude of difference between the blood pressure values in the upper limb and the lower limb of the left side body and the right side body, respectively. And the slopes of the side B1-C1 and side D1-A1 show a magnitude of difference between the blood pressure values in the upper limb and the lower limb of the right side body and the left side body, respectively. Therefore, a more symmetric rectangle 330 to the line 345 shows less variation in the blood pressure values in the left and right sides, and a rectangle 330 having a longer side A1-B1 than a side C1-D1, that is, having a trapezoidal shape to be tapered downward with an upper side longer than the lower side, shows there is a suspicion of stenosis in the lower limb.

In this way, the relationship between the blood pressure values in the left side and the right side, and the relationship between the blood pressure values in upper limb and lower limb can be understood in a moment. And reading the values of each vertex makes it possible to easily know each specific blood pressure value. Of course, the specific blood pressure values may be indicated as numeric values in correspondence with each plotted point.

(Simultaneous Presentation of Different Blood Pressure Values)

In measuring a blood pressure, usually a systolic blood pressure value, a diastolic blood pressure value, and a mean blood pressure value are measured. In the above example, a report which presents one of the blood pressure values is explained for better explanation and understanding, but a plurality of blood pressure values may be presented in a presenting region.

Figure 5:
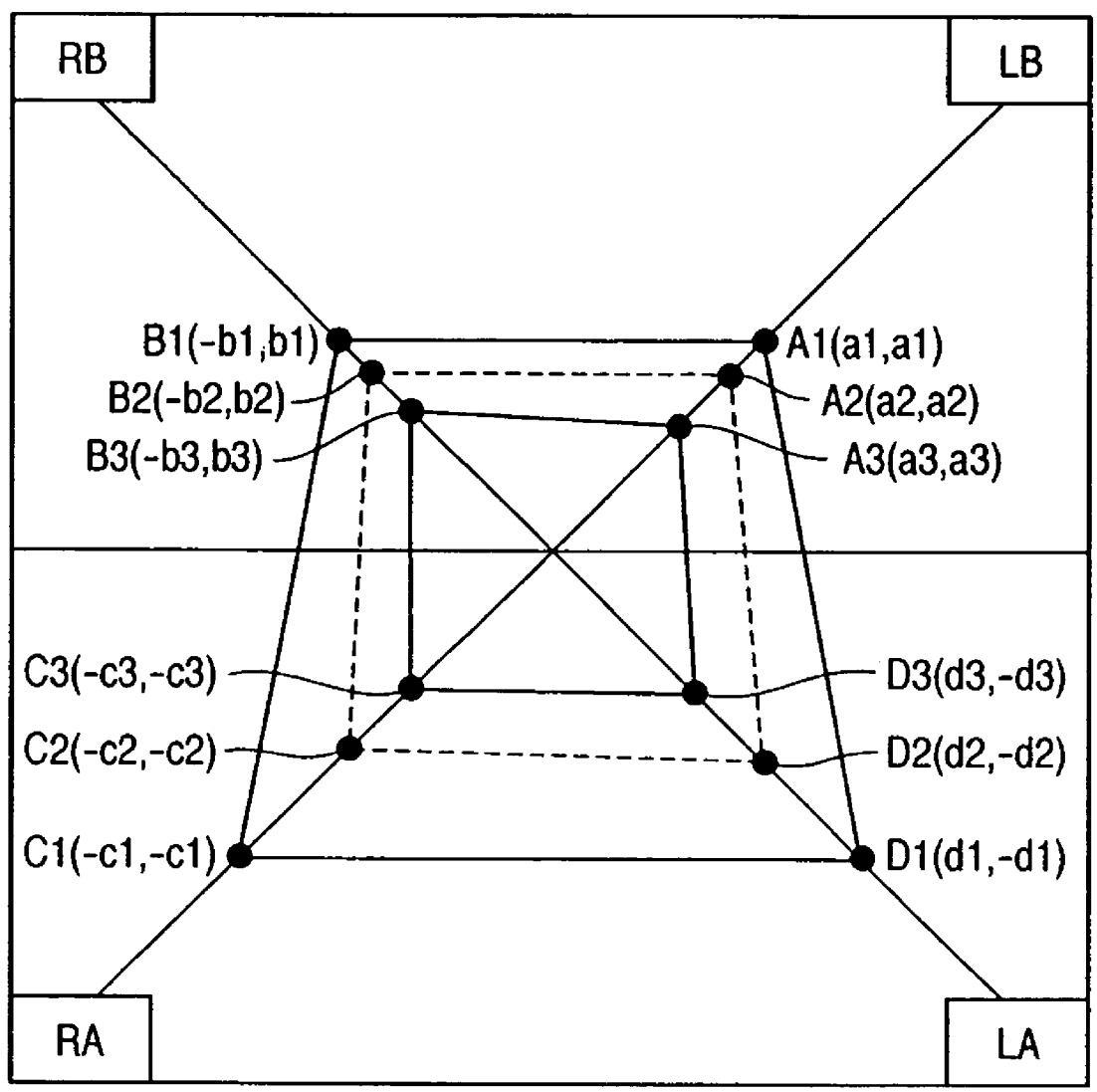

FIG. 5 is a diagram to show an example to present a systolic blood pressure value, a diastolic blood pressure value and a mean blood pressure value measured in each of four limbs according to the style of FIG. 4. In FIG. 5, a mean blood pressure value is expressed by a rectangle A2-B2-C2-D2, and a diastolic blood pressure value is expressed by a rectangle A3-B3-C3-D3, respectively.

(Supplemental Indicator)

Various supplemental indicators can be added to the basic bioinformation report described above.

(Indicator of Normal Range)

Figure 6A:
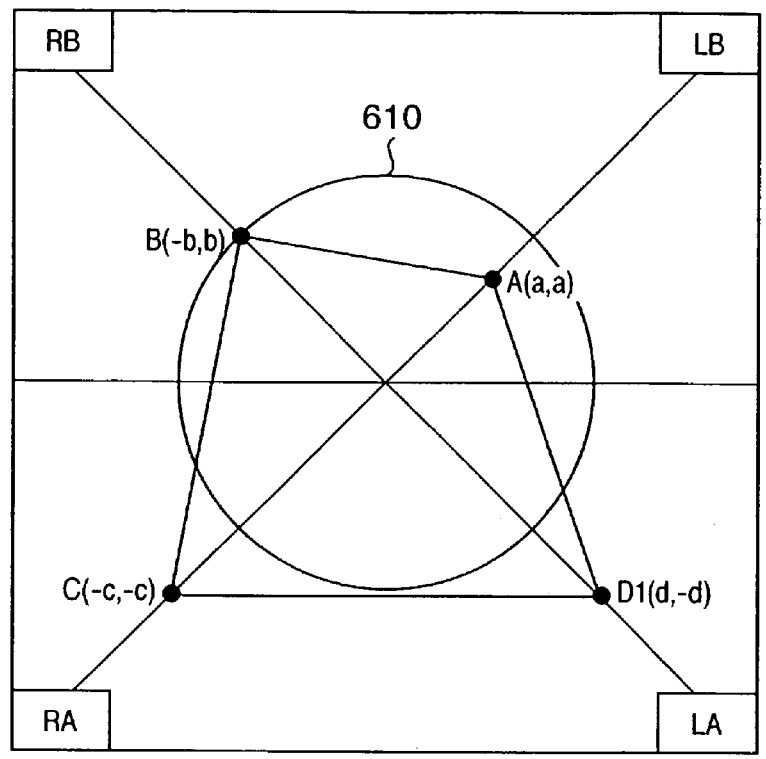
Figure 6B:
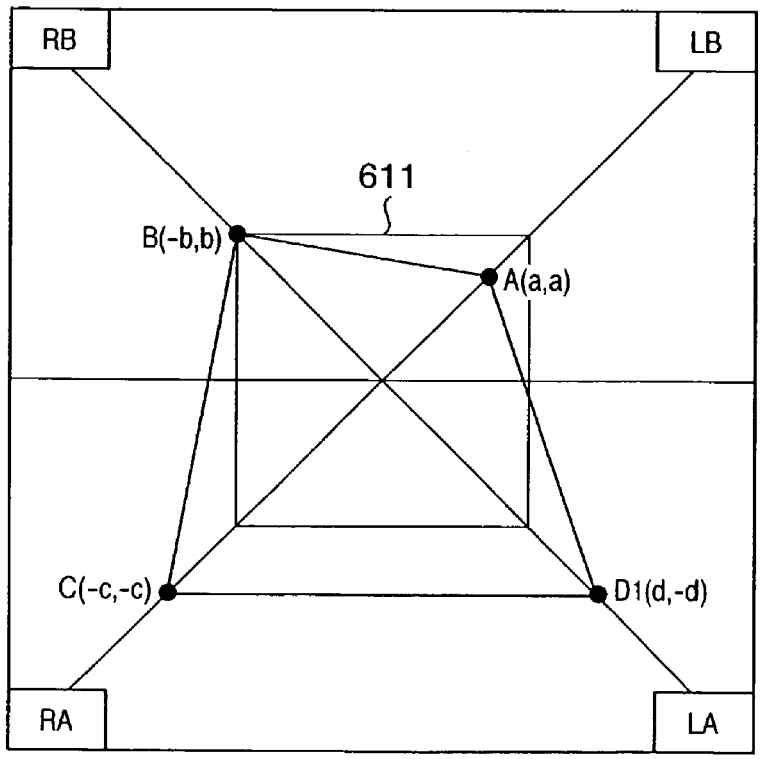

FIGS. 6A and 6B are diagrams to show an example of a bioinformation report in which indicators are added, on a basis of the blood pressure value in the upper right limb, to show a normal range for other blood pressure values. FIG. 6A shows an example added with a circle 610 through the coordinate (−b, b) of a blood pressure value in the upper right limb and centered at the origin O, and FIG. 6B shows an example added with a square 611 having a center point at the origin O and a vertex of the coordinate (−b, b). When the other blood pressure values, especially the blood pressure value in lower limb are inside of these indicators, there is a suspicion of stenosis in lower limb.

If the blood pressure value in upper limb is the basis of the indicator, the higher of blood pressure values in upper left and upper right limb is preferable used as the basis.

(Indicator to Illustrate the Difference Between Blood Pressures in Upper Limbs)

Figure 7:
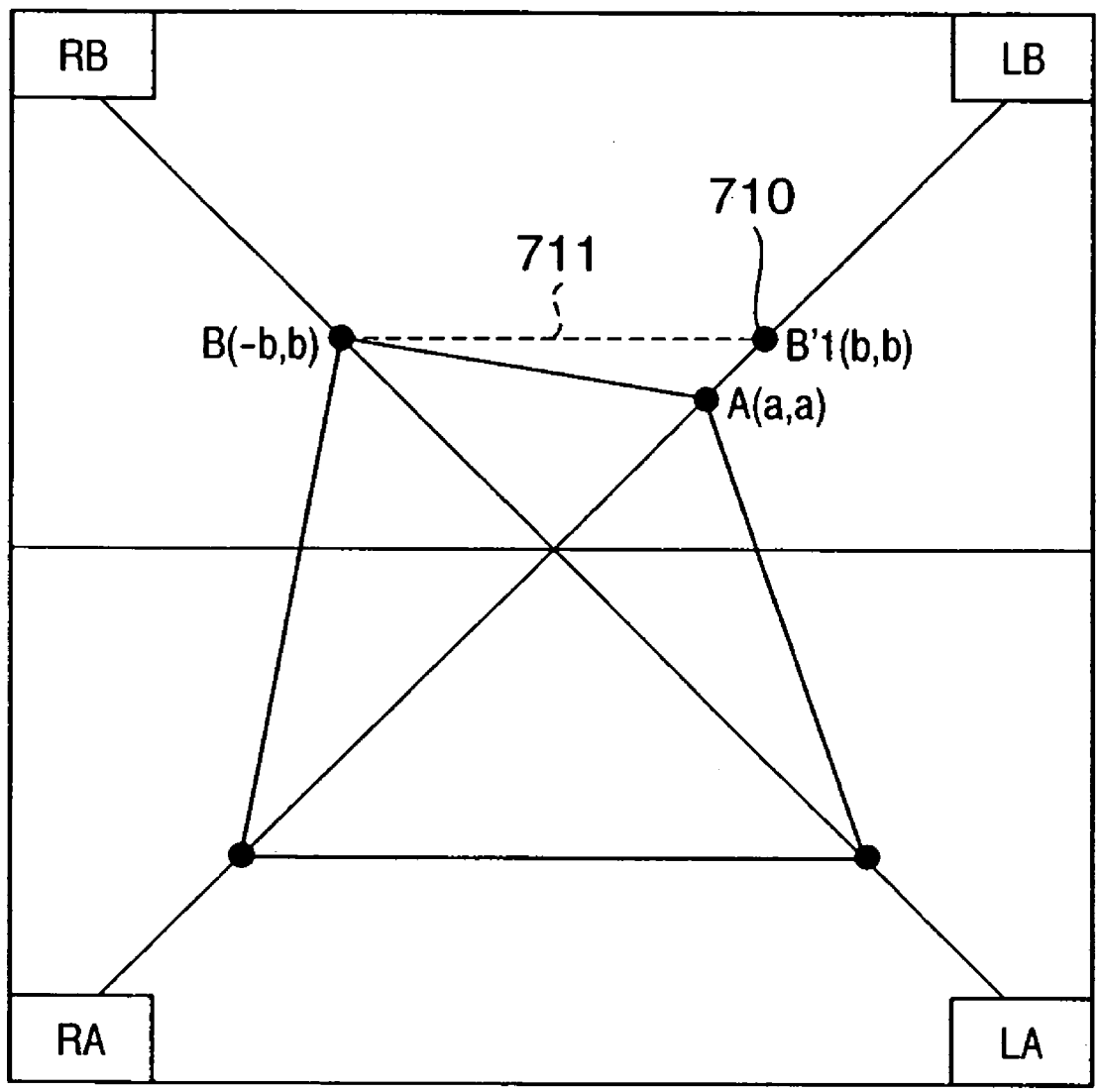

FIG. 7 is a diagram to show an example of a bioinformation report added with an indicator which illustrates a coordinate corresponding to the coordinate of the higher of the blood pressure values in upper limbs, that is the blood pressure values plotted on the first axis 325 and the second axis 326, on the axis on which the lower of the blood pressure values is plotted.

Because when there is a difference between the blood pressure values in left and right upper limbs, there might be a suspicion of hemodynamic insufficiency in the upper limb which showed the lower measured value, so this indicator is presented to evaluate the suspicion.

FIG. 7 is a diagram to show an example applied with this indicator in which the blood pressure value in the upper left limb is lower than the blood pressure value in the upper right limb. The indicator 710 is a mark illustrated on the axis on which the lower blood pressure value is plotted to show the coordinate corresponding to the higher blood pressure value. A line 711 may be also illustrated with the indicator, which extends horizontally toward the indicator 710 from the coordinate of the higher blood pressure value.

(Case with Blood Pressure Values not Normally Measured Due to Unmeasured or Unmeasurable Values)

In measuring a blood pressure, the above described rectangle cannot be imaged, when a measurement was not normally performed due to various factors, for example, a cuff being not appropriately attached, when an extreme measured value was obtained which is usually impossible (this is called to be unmeasurable), or when a measurement itself was not performed (unmeasured).

In the above case, in this embodiment, a deficient vertex to image a rectangle 330 composed of vertices of blood pressure values are will be compensated, and a rectangle 330 is imaged by using the compensated vertex. In order to distinguish the compensated vertex from the normally measured blood pressure values, the compensated vertices are indicated with different marks on axes for identification.

Figure 15:
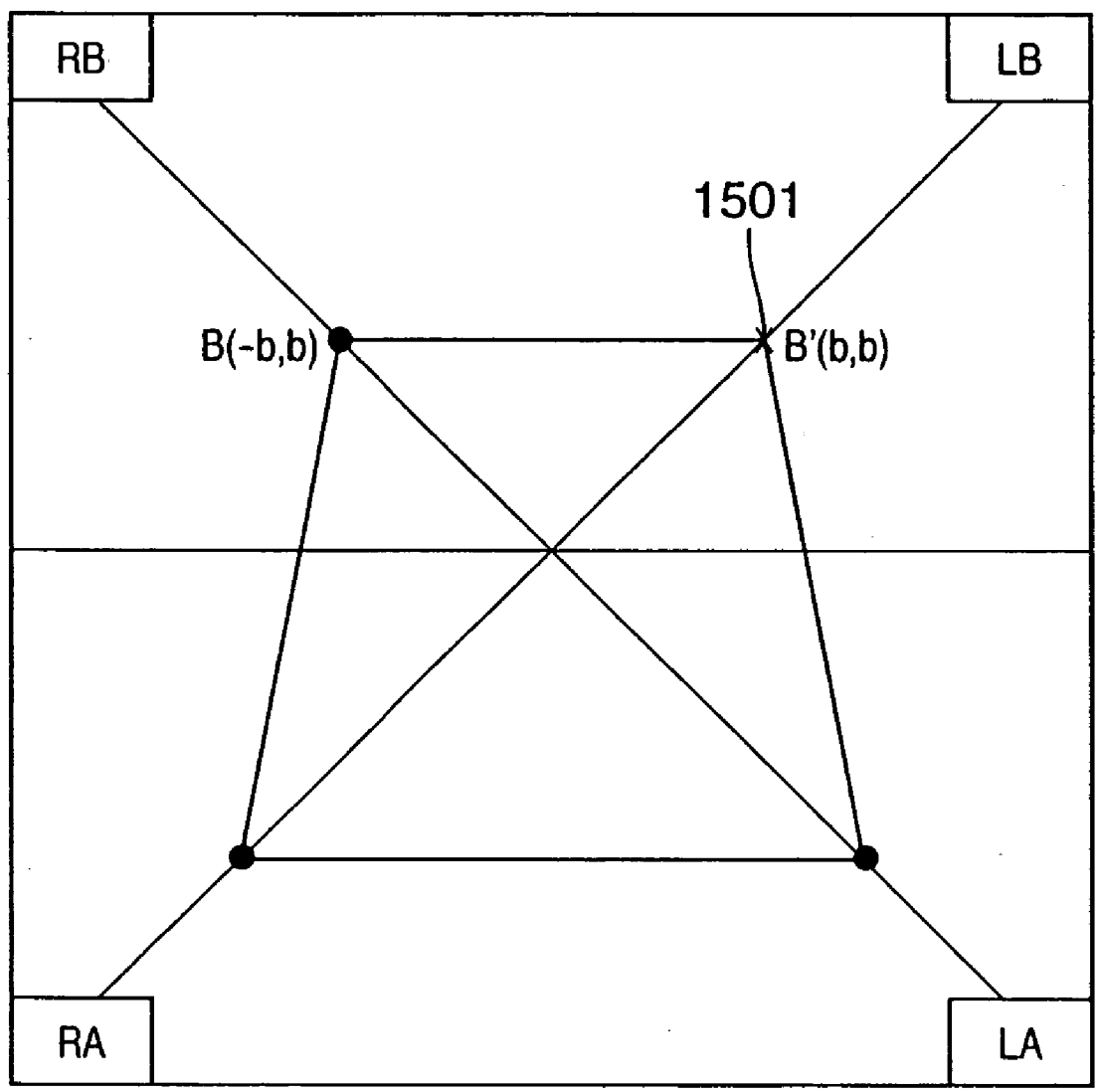
FIG. 15 is a diagram to explain a method to image a rectangle 330 by compensating a deficient vertex.

FIG. 15 shows an example in which when the blood pressure value to be plotted on the first axis 325 of the blood pressure values at upper limbs, that is the blood pressure values plotted on the first axis 325 and the second axis 326, was not obtained because it was not measured, or it was not measurable, the blood pressure value in the upper right limb which was obtained by a normal measurement and was plotted on the second axis is used as a value measured in upper left limb to be plotted on the first axis.

In FIG. 15, the mark 1501 to show the blood pressure value plotted on the first axis is "X", which allows it identified as a compensated point which is different from other plotted (measured) values.

In FIG. 15, an example is shown in which an upper limb blood pressure value is compensated, but similarly as for the blood pressure values in lower limbs, a coordinate corresponding to the blood pressure value which could be measured in one side of lower limb may be illustrated on the other side axis having no blood pressure value, so that the deficient vertex needed to image a rectangle can be compensated.

A letter or arrow may be used to illustrate which value is used to compensate the deficient vertex. Also, the line style (visual characteristics such as its width, color, solid line/dotted line) of the side contacting the indicator 1501 (the indicator 1501 is the beginning point or end point of the side) may be changed to be different from other sides of the rectangle 330.

(Indicators to Enhance Visibility)

Other than those described above, an indicator to enhance visibility may be added.

Figure 8A:
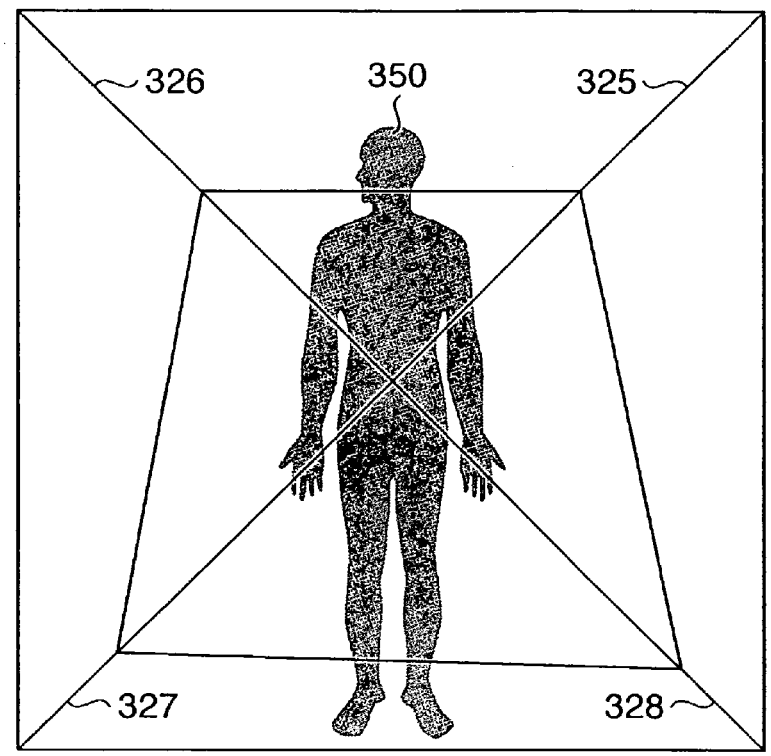

For example, as an indicator to illustrate measurement sites of plotted blood pressure values, an array of letters 341 to 344 may be added to visually discriminate the correspondences with each axis, or as shown in FIG. 8A, an image 350 of a human body may be added as a silhouette or a pattern illustrating a contour. Referring to FIG. 8A, it is intuitively understood that the blood pressure values plotted on the first to fourth axes 325 to 328 correspond to the blood pressure values in the left side and right side of upper limbs and lower limbs respectively. In order to make the correspondences between the axes and the blood pressure values clearer, a human body pattern with open arms and open legs may be used.

Figure 8B:
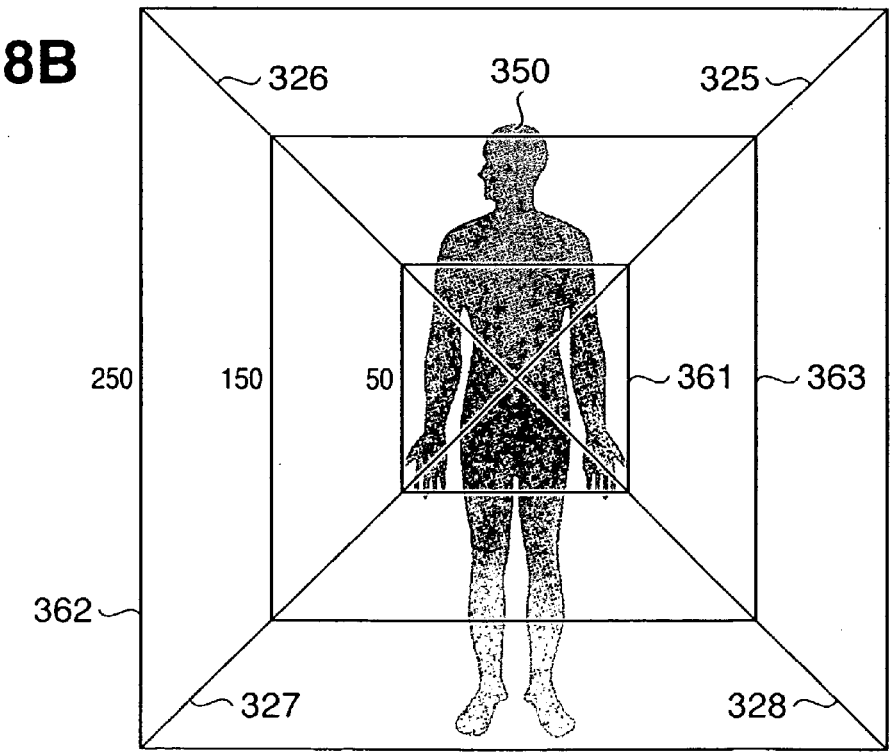

FIG. 8B shows an example in which the coordinates which show representative values on each axis are connected with a line as in the measured values. By illustrating the scales of representative values in this way, the rough values of the measured values may be understood. In FIG. 8B, the scales of representative values are expressed in a rectangle composed of vertices, which are determined by each coordinate, but the scales may be expressed by using a circle or an ellipse through each coordinate.

(Indicator to Show the Degree of Suspicion of Stenosis or Show the Site where there is a Suspicion of Stenosis)

As described above, though the shape of a rectangle 330 makes it easy to know if there is a suspicion of stenosis or not, an indicator other than the rectangle 330 to illustrate if there is a suspicion of stenosis or not, or an indicator to specifically illustrate in which site there is a suspicion of stenosis may be added.

Figure 9A:
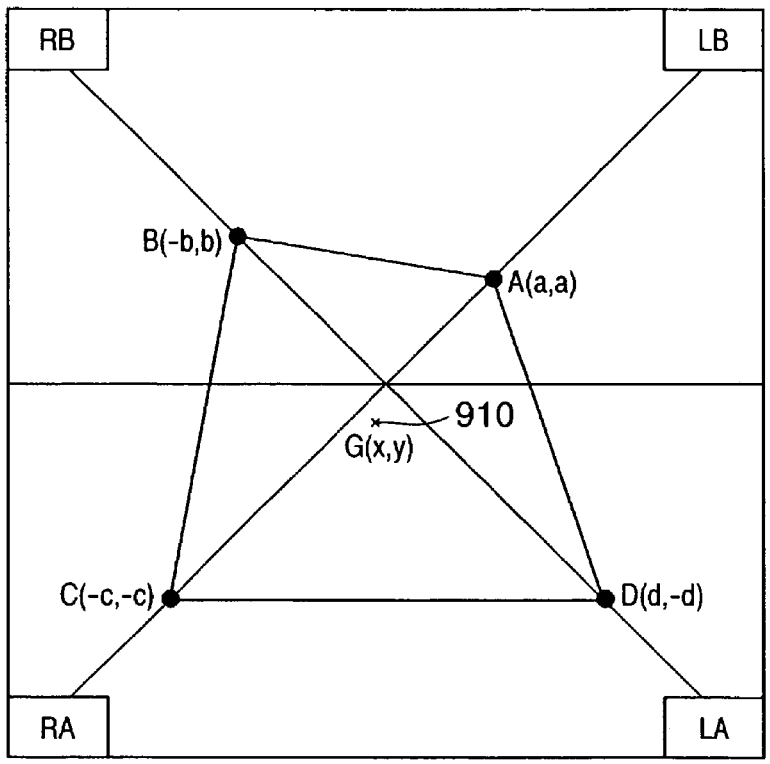

First, as an indicator to illustrate the degree of suspicion of stenosis, the position of a center point of the rectangle 330 may be positioned in the report. As described above, the closer to 1 the ratio between the blood pressure values in upper limb and lower limb is, and the less the difference between the blood pressure values in left side and right side is, the more the rectangle 330 features a rectangle, and the center point comes closer to the origin. Conversely, the farther the position of the center point of the rectangle 330 goes from the origin, the more there is suspicion of stenosis. FIG. 9A shows an example of a report in which the position of the center point of the rectangle 330 is illustrated with a mark 910 (in this example, X). In this embodiment, the position of the center point G (x, y) is determined as follows:

$$x = (-\text{blood pressure in right brachium} + \text{blood pressure in left brachium} - \text{blood pressure in right ankle} + \text{blood pressure in left ankle})/3\sqrt{2}$$

$$y = (\text{blood pressure in right brachium} + \text{blood pressure in left brachium} - \text{blood pressure in right ankle} - \text{blood pressure in left ankle})/3\sqrt{2}$$

Figure 9B:
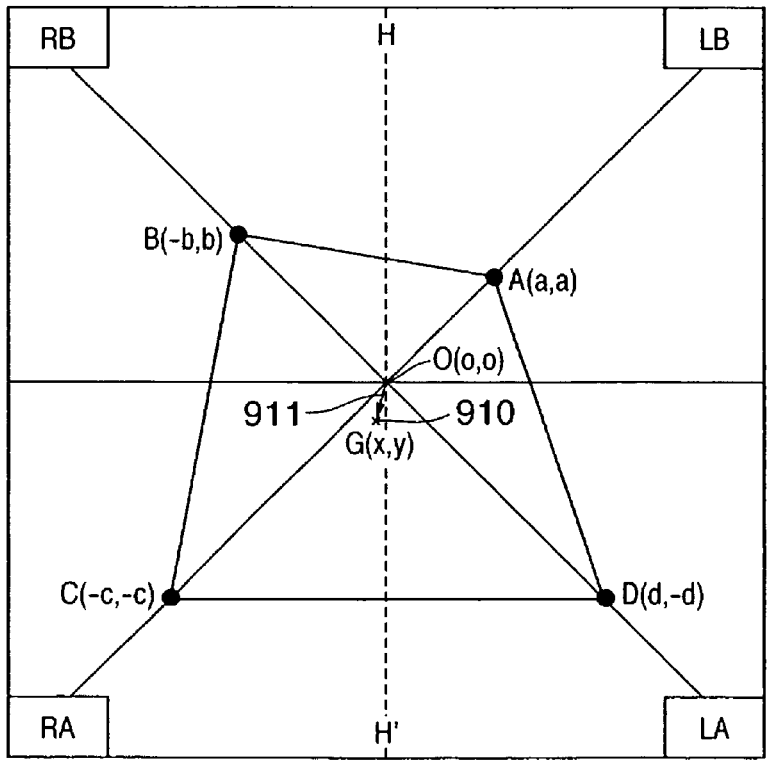

FIG. 9B shows an example of a report in which an arrow 911 from the origin toward the center point 910 is further added as an indicator to more clearly illustrate the position of the center point and the distance between the center point and the origin. The added arrow can indicate the degree of suspicion of stenosis by means of its length.

As another example of an indicator using the position of the center point, an indicator to illustrate the site under suspicion of stenosis may be added. This uses the fact that the site toward the contraposition to the center point is under suspicion of stenosis. And since the distance between a contraposition to the position of the center point and the origin corresponds to the distance from the position of the center point to the origin, the magnitude of the distance from the origin to the contraposition shows the degree of suspicion of stenosis.

Figure 10A:
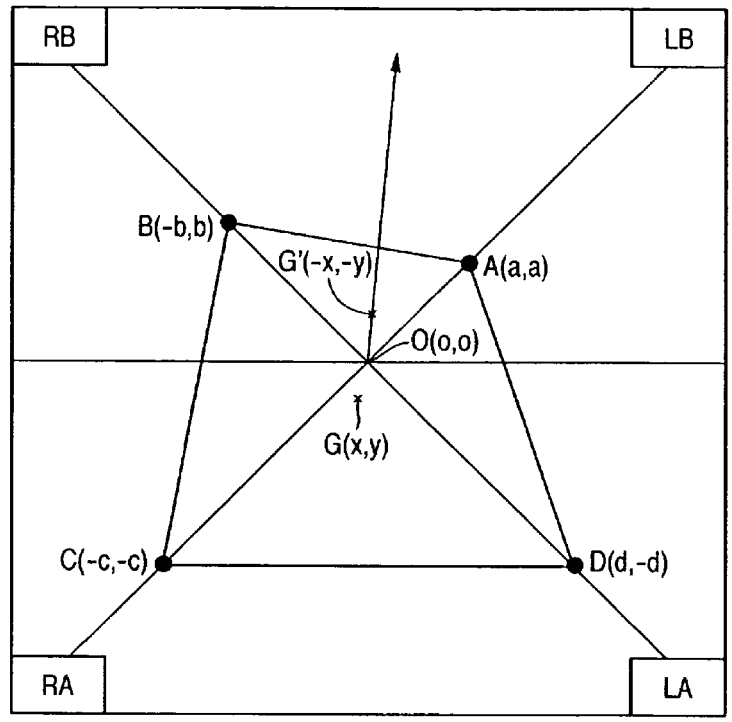

FIG. 10A shows an example of a report in which an arrow extending from the origin toward the contraposition of the center point 910 of the rectangle 330 is further added as an indicator to illustrate the site under suspicion of stenosis and the degree of suspicion of stenosis.

Figure 10B:
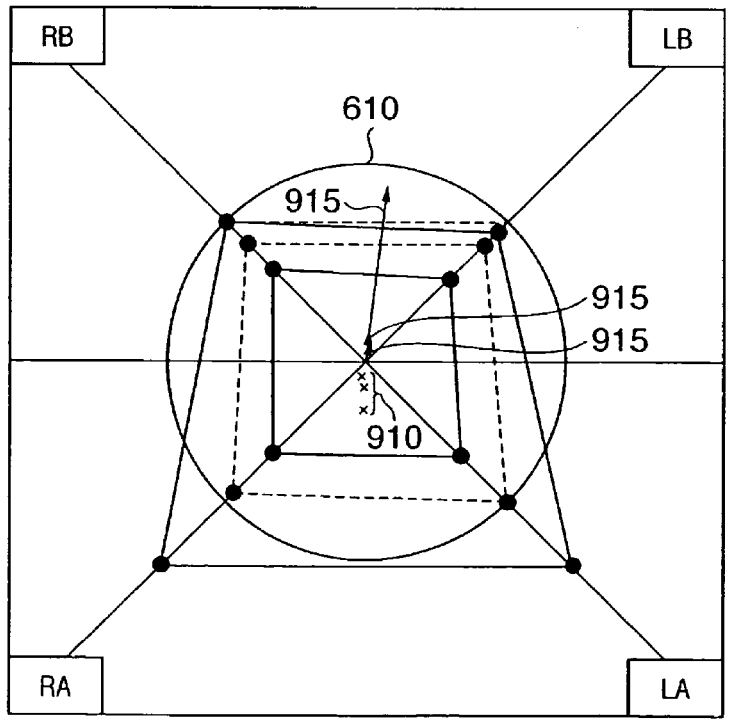

In FIG. 10A, an arrow extending a predetermined number of times that of the length between the origin and the contraposition (in this example, 10 times) is added to emphasize the meaning of the indicator. FIG. 10B shows an example of a report in which the simultaneous presentation of a plurality of blood pressure values described above with reference to FIG. 5, the indicator 610 to illustrate a normal range described above with reference to FIG. 6A, the position of the center points 910 for each of a systolic blood pressure value, a diastolic blood pressure value, and a mean blood pressure value, and the an arrow 915 extending a predetermined number of times that of the length between the origin and the contraposition to each of the position of the center points are applied in combination.

(ABI Indicator)

FIGS. 11A to 11C and FIGS. 12A to 12C are diagrams to show respectively an example of a report in which an indicator to illustrate the magnitude of an ABI is added. In the example shown in FIGS. 11A to 11C, a resultant vector 380 representing the sum of a vector extending from the origin to the coordinate of the blood pressure value in right (or left) upper limb and a vector from the origin to the coordinate of the blood pressure value in left (or right) lower limb is added as an indicator to illustrate a magnitude of an ABI.

That is, the angle θ between the vector 380 and the x axis 346 in an xy coordinate system with the common origin 321 (positive angles rotate counterclockwise) is determined as follows:

$$\theta[°]=\tan-1(1/ABI)-45$$

Figure 11A:
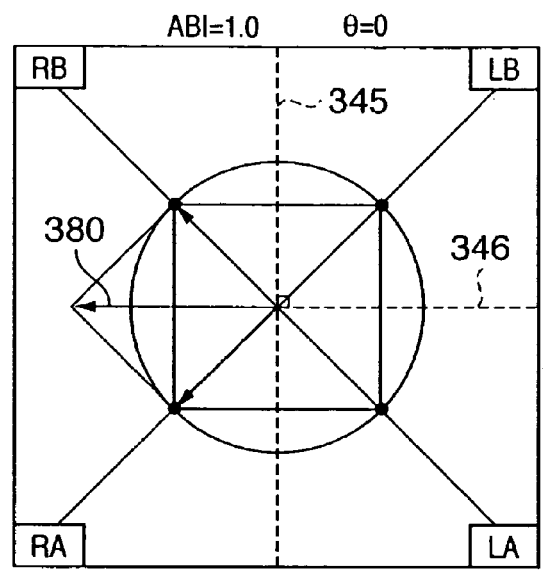
Figure 11B:
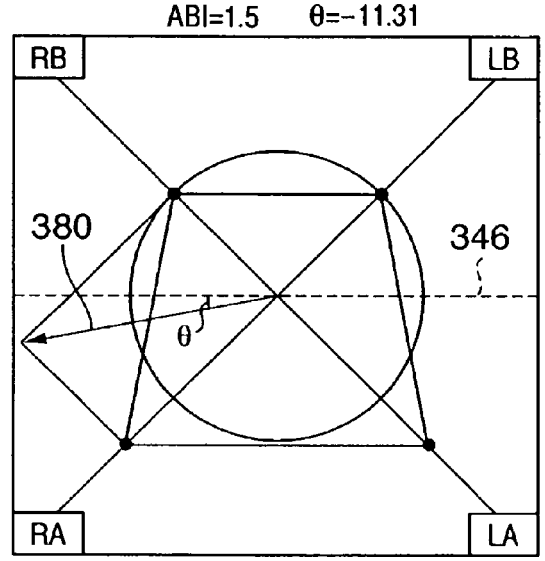
Figure 11C:
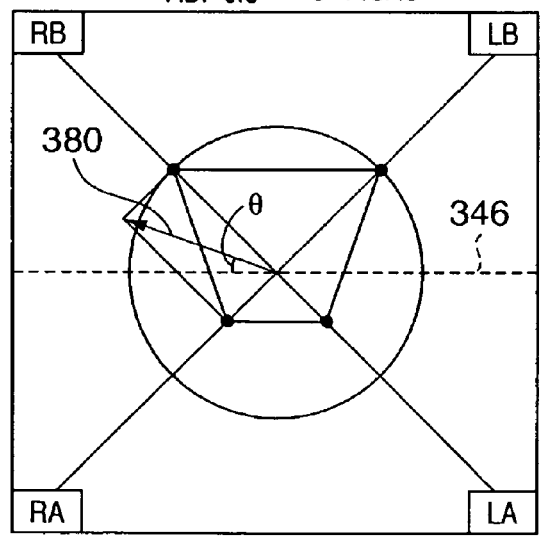

FIG. 11A shows a case with ABI=1.0, FIG. 11B shows a case with ABI=1.5, and FIG. 11C shows a case with ABI=0.5, where θ=0, θ=−11.31, and θ=18.43, respectively.

In the examples of FIGS. 11A to 11C, since each indicator is a resultant vector, larger blood pressure values provides a longer indicator.

Figure 12A:
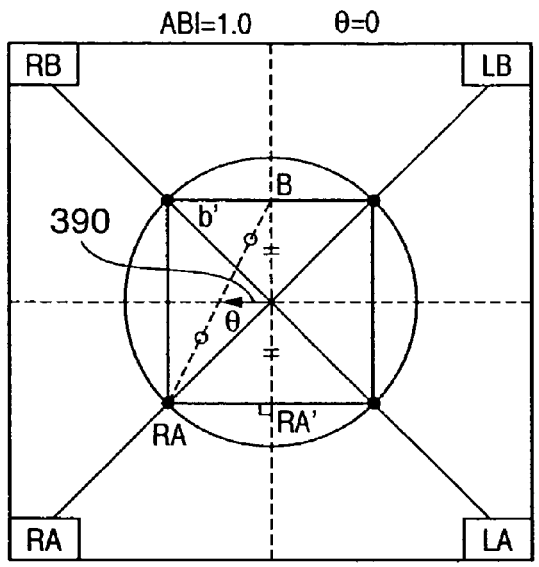
Figure 12B:
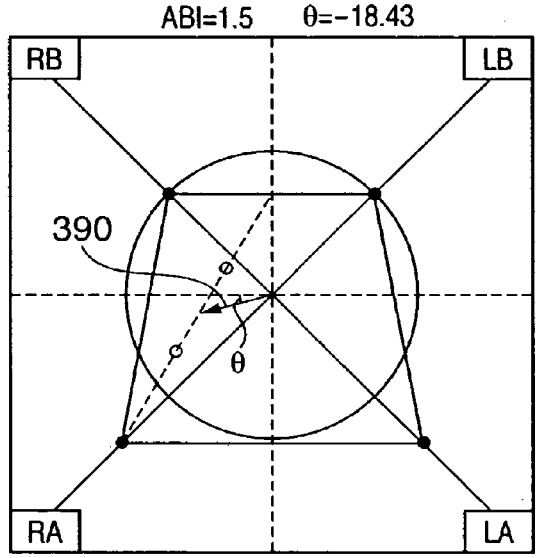
Figure 12C:
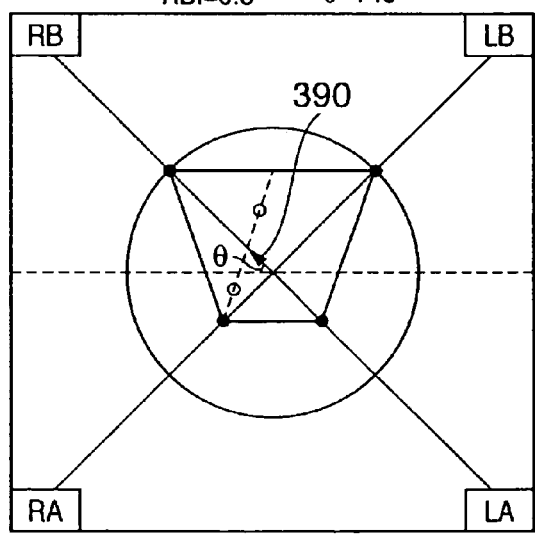

Similarly, in FIGS. 12A to 12C, a vector extending from the origin is used as an indicator, but the way to determine the angle θ and its size is different from the examples of FIGS. 11A to 11C.

In the example illustrated in FIGS. 12A to 12C, the angle θ is determined as follows:

$$\theta[°]=\tan-1(1/ABI-1)$$

The end point of the vector is defined as the center point on a straight line connecting an intersection of the y axis 345 and the straight line extended horizontally from the coordinate of the higher of the blood pressure values at upper limbs and the coordinate of one of the blood pressure values in lower limbs. This method may also achieve the illustration of an indicator which changes its angle depending on ABI.

FIGS. 12A to 12C show an indicator 390 when ABI is respectively 1.0, 1.5, and 0.5 as in FIGS. 11A to 11C.

FIG. 13 is a diagram to show an example in which a bioinformation report according to this embodiment is applied to a comprehensive report which includes other measurement results. In FIG. 13, the bioinformation report according to this embodiment is shown in the region 400. In the example illustrated in FIG. 13, to the report of FIG. 5 which presents a systolic blood pressure value, a diastolic blood pressure value and a mean blood pressure value, various indicators are applied such as representative scale indicators on each axis and a human body pattern, the position of a center point of a rectangle made up with systolic blood pressure values, an arrow extending from the origin toward the contraposition to the position of the center point.

Various indicators can be used in combination as needed, and any combination other than that shown in FIG. 13 may be, of course, used.

In this way, according to the present invention, plotting blood pressure values measured in four limbs on the first to fourth straight line axes extending from an origin into an upper right direction, an upper left direction, a lower left direction, and a lower right direction respectively, and laying out a rectangle composed of vertices which are determined by the plotted blood pressure values allow the specific measured value in each site to be easily known, and the relationships between the blood pressure values in four limbs to be intuitively understood from the shape of the rectangle. Thus, this is extremely useful as an indicator to determine any possibility of artery occlusion, and a site of occlusion, and the degree of occlusion.

Second Embodiment

Now, a bioinformation outputting device according to the second embodiment of the present invention will be explained. Because the bioinformation outputting device of this embodiment is the same as the device of the first embodiment except a report format to be output, only the report output format which is a feature of this embodiment will be explained.

The first embodiment in which the first axis 325 and the third axis 327, and the second axis 326 and the fourth axis 328 are drawn as a straight line respectively, is characterized in that the scales and/or directions of the straight line axes are different between upper limbs and lower limbs.

As described above, the slopes of the two longitudinal sides of the rectangle 330 are defined by the magnitude relationships between the blood pressure values in upper limbs and the blood pressure values in lower limbs, and for example, when the slope of the side B1-C1 is negative, it means that the blood pressure value in lower right limb (ankle)/the blood pressure value in the upper right limb (brachium) is less than 1. Because this ratio is namely an ABI itself, the slope of the longitudinal sides of the rectangle 330 can suggest an ABI value.

Based on the above concept, the scaling or slopes of axes (which can be considered as a direction from the origin or the angle between the line 345) may be adjusted to make the slope of longitudinal sides of a rectangle go positive or negative across the border of an abnormal ABI value. In other words, the scaling or slopes of axes are adjusted so that the rectangle has a square-like shape when the relationship between the blood pressure values measured in an upper left limb, an upper right limb, a lower left limb and a lower right limb is within a normal range. This adjustment enables an evaluation on a suspicion of stenosis in a lower limb by glancing at the slope of longitudinal sides of the rectangle 330.

Specifically, when the blood pressure value in lower limb/the blood pressure value in upper limb is equal to a threshold value (e.g., 0.9), the direction and/or scaling of the axes may be adjusted so that the side connecting the blood pressure values is parallel to the line 345 (the slope is infinite). More specifically, the slope and/or scaling of axes may be adjusted so that the magnitudes of the horizontal coordinate components of the plotted blood pressure values are the same.

For example, this adjustment is performed on the basis of the blood pressure value in the upper right limb and the blood pressure value in the lower right limb (or the blood pressure value in the upper left limb and the blood pressure value in the lower left limb) in the example of FIG. 4. And assume that the blood pressure value in the upper right limb is 120 mmHg.

In this case, the above control can be achieved by changing the scaling or slope (direction) of the third axis 327 on which the blood pressure value in the lower right limb is plotted as shown in FIGS. 14A and 14B. FIG. 14A shows a case in which the scaling of the axis is changed while the slope being the same. That is, the scaling of scales of the axis 327 is changed so that, when the blood pressure value in upper limb is 120, at the position where a straight line extending downward from the coordinate of the blood pressure value intersects with the third axis 327, the third axis represents the value 108 which is the product of multiplying 120 by the threshold value 0.9. If the blood pressure value in lower limb is less than 108, the slope of the side B1-C1 goes negative, thereby the shape of the rectangle enables the evaluation that there is a suspicion of stenosis in the lower limb.

Alternatively, the similar control can be achieved by changing the slope of an axis while the scaling of the axis being the same. FIG. 14B shows a case, on the same condition as FIG. 14A, in which the similar control is achieved without changing the scaling of an axis, by setting the slope β of the third axis 327 larger than the slope α of the second axis 326 to make the increase of the x axis components of points on the third axis 327 increase more than those on the second axis 326.

The blood pressure value in lower limb may be set as the basis to achieve the above described control on the axis for the blood pressure value in upper limb. Alternatively, both axes may be adjusted, or adjustment of slope and adjustment of scaling may be used in combination.

In this way, a bioinformation outputting device according to this embodiment is more effective for easy evaluation based on a shape of the rectangle than a bioinformation report of the first embodiment. In this embodiment also, needless to say, a plurality of blood pressure values such as those shown in FIG. 5 may be presented, and various supplemental indicators described in the first embodiment may be applied in combination as needed.

Third Embodiment

As an indicator to indicate the degree of suspicion of stenosis or a site under suspicion of stenosis, the difference or the magnitude of a ratio between the blood pressure values in left and right upper limbs, and the indicator with respect to an ABI may be used in combination.

Figure 16A:
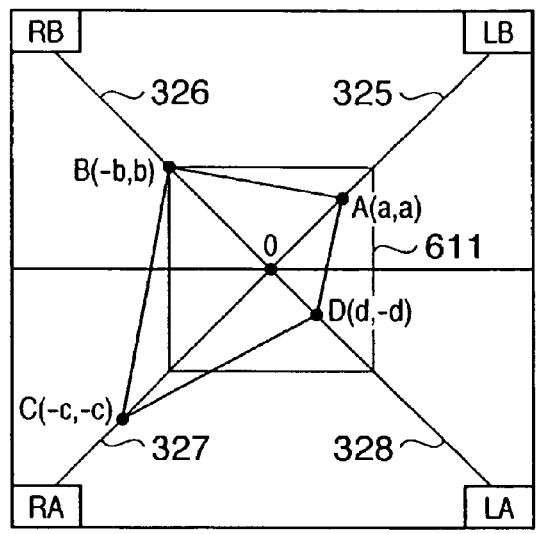
FIGS. 16A to 16C and FIGS. 17A to 17C are diagrams to explain an indicator according to a third embodiment of the present invention.
Figure 16B:
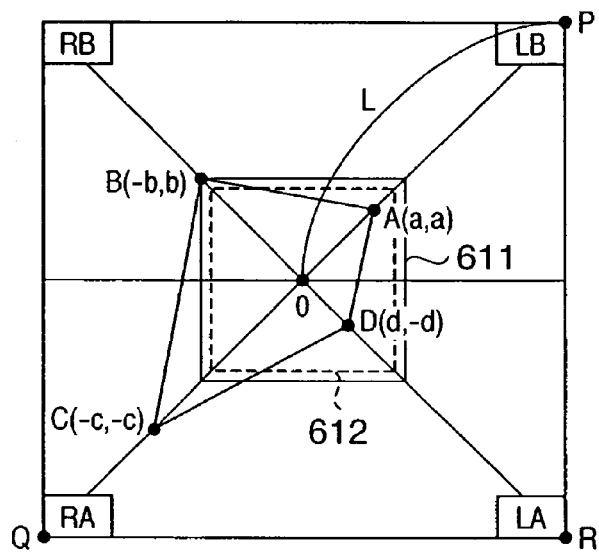
Figure 16C:
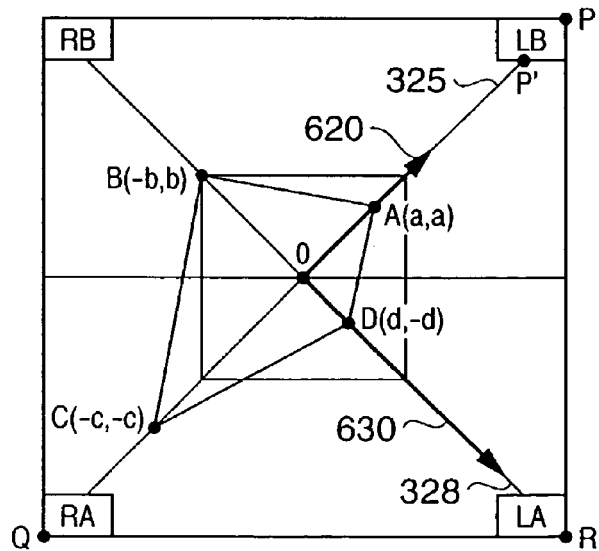

FIGS. 16A to 16C explain a method to add an indicator according to this embodiment. FIG. 16A shows an example of a bioinformation report in which, on a basis of the blood pressure value in the upper right limb, a square 611 is added as an indicator to illustrate a normal range for other blood pressure values, as in FIG. 6B, the square 611 having a vertex at the coordinate (−b, b) and the origin O as the center point.

In this embodiment, the following two are used as the added conditions for an indicator to illustrate the degree of suspicion of stenosis or a site under suspicion of stenosis:
(1) the difference between the blood pressure values in the left and right upper limbs is a predetermined value or more (e.g., 20 mmHg or more), and
(2) the ABI of the left or right side is less than 1.00.

When one of these conditions is satisfied, an indicator is added to a report.

In this embodiment, when the condition (1) is satisfied, on the first or second axis 325, 326 corresponding to the upper limb in which the lower blood pressure value was measured, an arrow which extends from the origin O and has a length having a positive relationship with the magnitude of difference between blood pressures is added as an indicator to illustrate the degree of suspicion of stenosis or a site under suspicion of stenosis.

FIG. 16A shows a report after adding an indicator 612 illustrating a range, which satisfies the condition (1) to FIG. 16A. For example, when a condition in which the absolute value of a difference between the left and right blood pressures is 20 mmHg or more is applied, a square is added which corresponds to a value 20 mmHg lower than the basic blood pressure value in upper limb (that is, usually, the higher blood pressure value, and in this example, the blood pressure value in the upper right limb).

In the example of FIG. 16B, the condition (1) is satisfied because the blood pressure value in the upper left limb is inside of the indicator 612.

In this case, an arrow which extends outward from the origin O along the first axis 325 is added as an indicator. The larger the difference between the left and right blood pressures is (the worse the condition is suspected), the longer the arrow is. Specifically, a length of the arrow is determined as follows: where L is the distance from the origin O to a vertex P, $$L \times (1 - \text{the lower blood pressure value in the left or right upper limb/the higher blood pressure value in the left or right upper limb} + \alpha)$$

where α is a positive constant less than 1. The constant α functions to adjust so that the maximum value of the blood pressure difference which can be actually observed is illustrated as a sufficient long indicator.

Alternatively, the length of the arrow may be determined depending on a value actually obtained, by assigning the practical maximum value and minimum value (of the lower systolic blood pressure value in the left or right upper limb/the higher systolic blood pressure value in the left or right upper limb), which is assumed when the condition (1) is satisfied, to the origin O and the vertex P.

When there are the marks which mean the sites ([LB], [RB], [RA], [LA]) at vertex as shown in FIGS. 16A to 16C, the minimum value may be assigned to the position (e.g. P') where an axis is closest to a vertex.

FIG. 16C shows an example of an indicator 620 which is added when the condition (1) is satisfied. The length (magnitude) of the indicator 620 makes it possible to be intuitively understood that the blood pressure in the upper left limb is significantly low compared to the blood pressure value in the upper right limb and that to what degree stenosis is under suspicious (how large the difference is).

Next, addition of an indicator according to the condition (2) will be explained. Unlike the condition (1), the condition (2) can be assessed for the left and right side separately, and here also, the condition (2) is explained to be assessed for the left and right side separately, but the condition (2) may be assessed only for an ABI in right side of the body or left side of the body.

The condition (2) is whether or not an ABI is less than 1.00. Thus, when an ABI in right side of the body or left side of the body is less than 1.00, an indicator which is longer (larger) in correspondence to a smaller value is added on an axis for the corresponding lower limb.

For example, an ABI in left side of the body is less than 1.00, an indicator similar to that when the condition (1) is satisfied is added on the fourth axis 328 which corresponds to the lower left limb.

The length of the indicator may be determined depending on a value actually obtained, by assigning 1 and the assumable and practical maximum value (e.g. 0.5) to the origin O and the vertex Q (or R). However, in this case, since the indicator is often too short to be assessed when an ABI is close to 1, an indicator deformed to correspond a values lower than the actual value is used when an ABI is close to 1.

For example, in the case of 1.00>ABI>0.9, an indicator is added by setting the ABI=0.9. The indicator may be a dotted line to visually illustrate that the indicator is deformed.

In FIG. 16C, the ABI in the right side of the body is 1.00 or more, but the ABI in the left side of the body is less than 1.00, and an arrow 630 which extends outward from the origin O is added on the fourth axis 328 which corresponds to the lower left limb.

A report ultimately added with an indicator (620 or 630) according to the conditions (1), (2) will do, and the indicator 611 to illustrate a normal blood pressure range, the indicator 612 to illustrate an abnormal range of a difference between the left and right blood pressure values may not be added to an ultimate report.

Figure 17A:
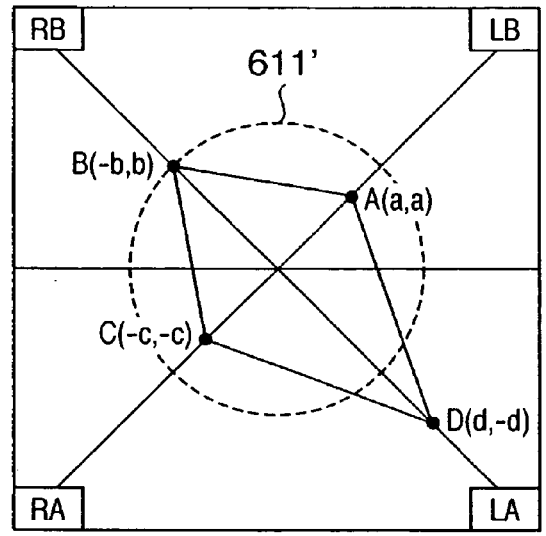
Figure 17B:
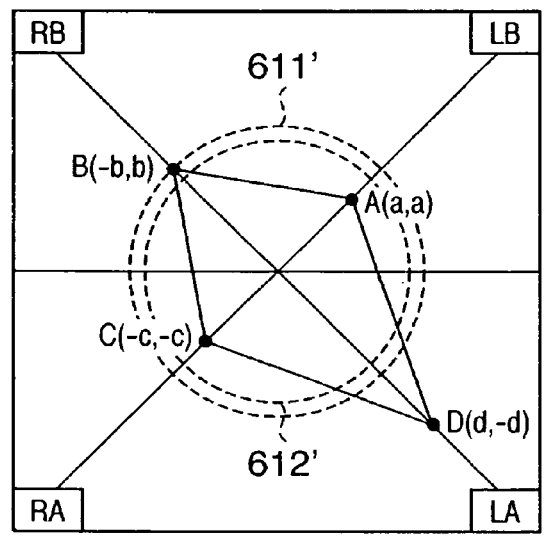
Figure 17C:
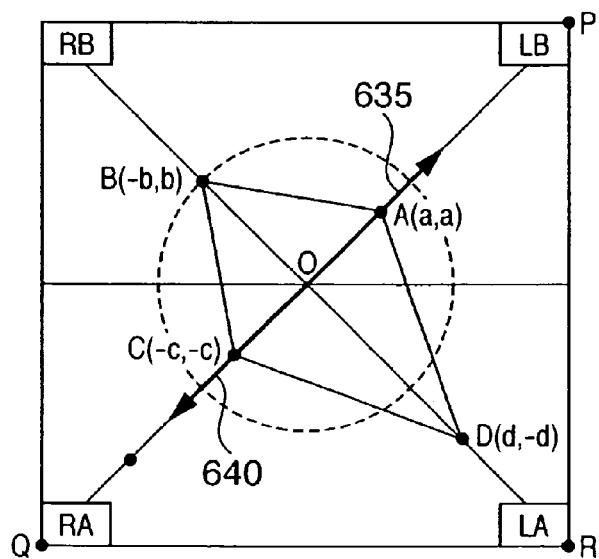

FIGS. 17A to 17C show modified examples according to this embodiment, and the indicator 611 and the indicator 612 are illustrated as circles as shown in FIG. 6A. FIGS. 17A to 17C correspond to FIGS. 16A to 16C, respectively.

The positions and lengths of the ultimately added indicator in FIGS. 17A to 17C are different from FIGS. 16A to 16C due to the different blood pressure values to be plotted, but the indicators 635, 640 are added according to the method described above with reference to FIGS. 16A to 16C. The examples of FIGS. 17A to 17C show that the ABI in the right side of the body is low, and the blood pressure in the upper left limb is lower than the blood pressure in the upper right limb by a predetermined value or more.

In this way, in this embodiment, the magnitude of difference between the blood pressure values in the left and right upper limb and an indicator with respect to an ABI are added together as indicators to illustrate the degree of suspicion of stenosis or a site under suspicion of stenosis, which allows a rough idea about a site under suspicion of stenosis or the degree of suspicion to be caught in a moment.

The indicators described in this embodiment can be added to any style of a report explained in the above first and second embodiments. For example, the human body pattern as shown in FIGS. 8A and 8B or the scales of representative values along axes may be added, or a diastolic blood pressure value or a mean blood pressure value as well as a systolic blood pressure value may be plotted. Any combination with other added indicators may be used.

Figure 18:
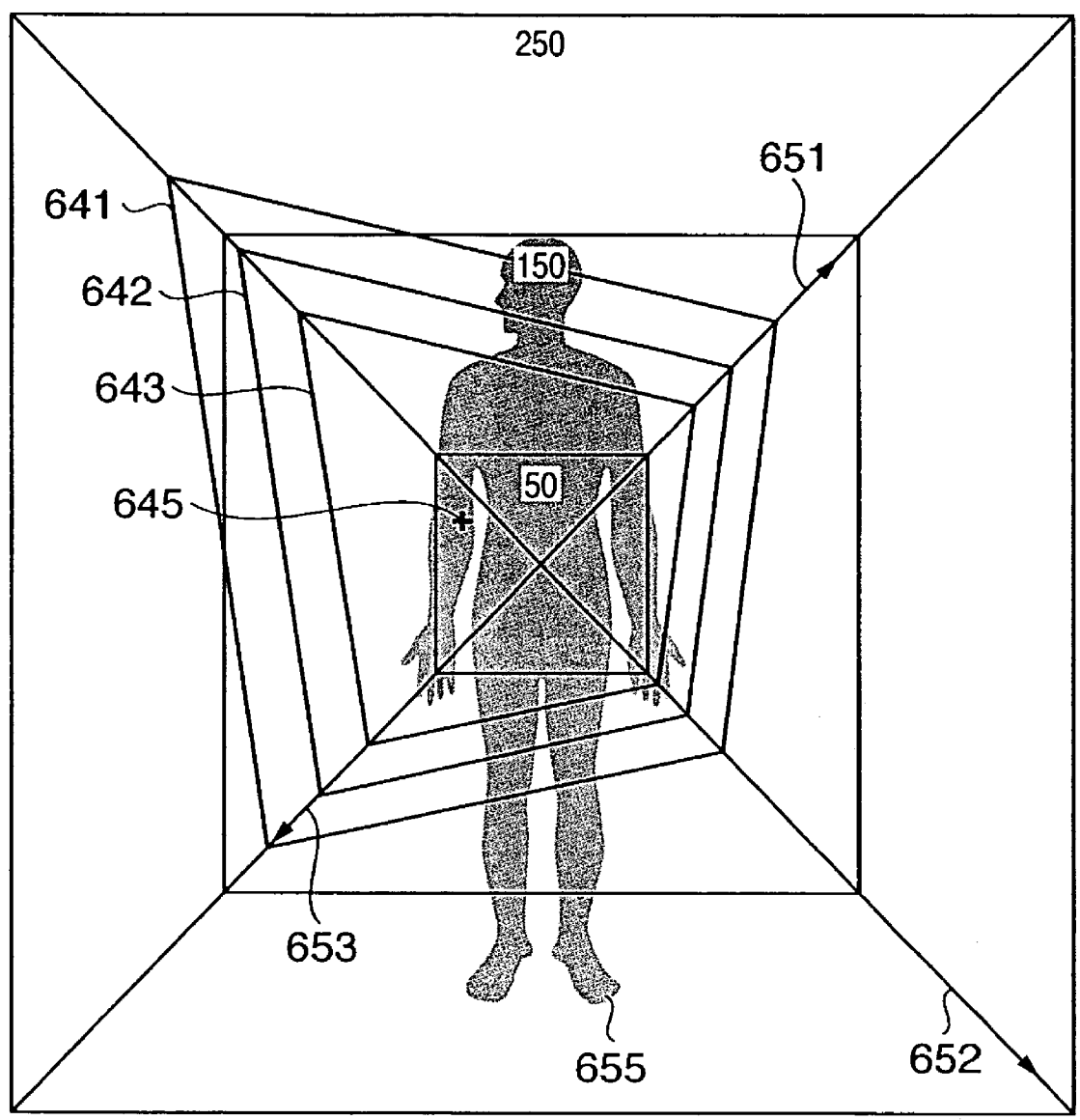
FIG. 18 is a diagram to show an example in which the systolic blood pressure value 641, the mean blood pressure value 642, and the diastolic blood pressure value 643 are plotted, and the center point of blood pressures 645 explained with reference to FIGS. 9A and 9B, and the indicators 651 to 653 in this embodiment are applied to the report format shown in FIG. 8B.

FIG. 18 is a diagram to show an example in which the systolic blood pressure value 641, the mean blood pressure value 642, and the diastolic blood pressure value 643 are plotted, and the center point of blood pressures 645 explained with reference to FIGS. 9A and 9B, and the indicators 651 to 653 in this embodiment are applied to the report format shown in FIG. 8B.

FIG. 19 is a diagram to show an example in which the bioinformation report of FIG. 18 is applied to a comprehensive report which includes other measurement results. In the example shown in FIG. 19, since the ABI in the left side of the body is 0.78, an indicator 660 according to this embodiment is added. More information is illustrated than that in the comprehensive report shown in FIG. 13, such as an estimated value in vascular age and a history of measured values.

Other Embodiment

The report outputting process in each above described embodiment may be performed, for example, with a computer device which reads the blood pressure values measured in advance out of a memory which stores the values, and outputs a report of an above described style. Therefore, needless to say, any program which makes the computer device execute the report outputting process in each above described embodiment, or any computer readable recording medium which stores the program are also included in the present invention.

Also, any recording medium such as a printing paper which has a region to print out the above described bioinformation report, for example, a region printed in advance with at least one of the first to fourth axes, the human body pattern shown in FIGS. 8A and 8B, the scales of representative values along the axes, the letters 341 to 344 of FIG. 4 are all also included in the present invention.

The blood pressure value may be measured with any method including, but not limited to, a method other than oscillometric method, for example, a method using Korotkov sound, ultrasound, or light, or an invasive measuring method.

The display formats of the various above described report and the measurement results to be included in a report may be configured to be selectable by user, or the scaling of a graph may be configured to be changeable by user.

As many apparently widely different embodiments of the present invention can be made without departing from the spirit and scope thereof, it is to be understood that the invention is not limited to the specific embodiments thereof except as defined in the claims.

What is claimed is:

1. A bioinformation outputting device, comprising:
obtaining unit that obtains blood pressure values measured in four limbs;
layout unit that generates a report which presents the blood pressure values in a common two dimensional region; and
outputting unit that outputs the report;
and wherein the report comprises a blood pressure value presenting region which has first to fourth linear axes extending in an upper right direction, an upper left direction, a lower left direction, and a lower right direction respectively from an origin, the first and the second axes being arranged to be symmetrical to each other relative to a straight line running straight through the origin from top to bottom of the report, and the third and the fourth axes being arranged to be symmetrical to each other relative to the straight line, wherein
a blood pressure value measured in an upper left or upper right limb is plotted on the first axis;
a blood pressure value measured in an upper right or upper left limb is plotted on the second axis;
a blood pressure value measured in a lower limb on the same side as that for the blood pressure value plotted on the second axis is plotted on the third axis;
a blood pressure value measured in a lower limb on the same side as that for the blood pressure value plotted on the first axis is plotted on the fourth axis; and
a rectangle composed of vertices which are determined by the blood pressure values plotted on the first to fourth axes is illustrated.

2. The bioinformation outputting device according to claim 1, wherein the layout unit generates the report in which at least two kinds of a systolic blood pressure value, a diastolic blood pressure value and a mean blood pressure value are plotted on the first to fourth axes, and at least two rectangles, each of which is determined by same kind of blood pressure values, are illustrated.

3. The bioinformation outputting device according to claim 1, wherein the layout unit generates the report further comprising an indicator to illustrate, on the basis of one of the blood pressure values measured in the upper left limb, the upper right limb, a lower left limb and a lower right limb, and a normal range of the other three blood pressure values.

4. The bioinformation outputting device according to claim 1, wherein the layout unit generates the report in which the first axis and the third axis, and the second axis and the fourth axis are drawn as a straight line respectively.

5. The bioinformation outputting device according to claim 1, wherein the layout unit generates the report in which the first axis and the third axis, and the second axis and the fourth axis are drawn as a straight line respectively, and these two straight lines are orthogonal to each other.

6. The bioinformation outputting device according to claim 1, wherein the layout unit determines a scaling of the first to fourth axes so that the rectangle has a square-like shape when the relative relationship among the blood pressure values measured in the upper left limb, the upper right limb, a lower left limb and a lower right limb is within a normal range.

7. The bioinformation outputting device according to claim 1, wherein the layout unit generates the report in which the first to fourth axes have same scales and a same range.

8. The bioinformation outputting device according to claim 1, wherein the layout unit generates the report further comprising an indicator to illustrate a coordinate, corresponding to a higher one of the blood pressure values plotted on the first axis and the second axis, on the axis on which a lower one of the blood pressure values is plotted.

9. The bioinformation outputting device according to claim 1, wherein when it is determined that one of the blood pressure values to be plotted on the first axis and the second axis was not normally measured, the layout unit generates the report in which the other blood pressure value is plotted as a measured value as the one of the blood pressure values.

10. The bioinformation outputting device according to claim 1, wherein when it is determined that one of the blood pressure values to be plotted on the third axis and the fourth axis was not normally measured, the layout unit generates the report in which the other blood pressure value is plotted as a measured value as the one of the blood pressure values.

11. The bioinformation outputting device according to claim 1, wherein the layout unit generates the report further comprising an image of a human body is in the blood pressure value presenting region so that correspondences between positions where the blood pressure values to be plotted on the first to fourth axes are measured can be recognized.

12. The bioinformation outputting device according to claim 1, wherein the layout unit generates the report further comprising an arrow in the blood pressure value presenting region, the arrow having a size and a direction depending on the relation between a blood pressure value in an upper limb and the blood pressure value in the lower limb which are plotted on the same right or left side.

13. The bioinformation outputting device according to claim 12, wherein the layout unit generates the report in which the arrow has the direction defined by a ratio between the blood pressure value in the upper limb and the blood pressure value in the lower limb which are plotted on the same right or left side, and the size defined by the blood pressure value in the upper limb and the blood pressure value in the lower limb which are plotted on the same right or left side.

14. The bioinformation outputting device according to claim 12, wherein the layout unit generates the report in which the arrow has a beginning point at the origin and is illustrated as a resultant vector representing a sum of vectors having end points determined by respective blood pressure values in the upper limb and the blood pressure value in the lower limb which are plotted on the same right or left side.

15. The bioinformation outputting device according to claim 12, wherein the layout unit generates the report in which:
the arrow has a beginning point at the origin; and
the arrow is illustrated so that the arrow has an end point at a middle point of a straight line connecting an intersection between a straight line extending upward vertically from the origin and a straight line extending horizontally from a coordinate corresponding to the higher of the blood pressure values in the upper limbs and a coordinate of the blood pressure value in the lower limb.

16. The bioinformation outputting device according to claim 1, wherein the layout unit generates the report further comprising an arrow which has a beginning point at the origin and extends in a direction toward a contraposition to a barycenter of the rectangle.

17. The bioinformation outputting device according to claim 1, wherein, when a magnitude of a difference between the blood pressure values in the upper right limb and the upper left limb is a predetermined value or more, the layout unit generates the report further comprising an indicator, which has a length depending on either the magnitude of the difference or a magnitude of a ratio between the blood pressure values in the upper right limb and the upper left limb, on the one of the first and the second axes on which a lower one of the blood pressure values in an upper limbs is plotted, with a beginning point at the origin.

18. The bioinformation outputting device according to claim 17, wherein the layout unit generates the report in which the smaller the ratio is or the larger the difference is, the longer the indicator is.

19. The bioinformation outputting device according to claim 1, wherein, when a ratio between the blood pressure values in an upper limb and the lower limb plotted on the same right or left side is an abnormal value, the layout unit generates the report further comprising an indicator having a length depending on the value of the ratio and a beginning point at the origin on one of the third and the fourth axis on which the blood pressure values in the lower limbs are plotted.

20. The bioinformation outputting device according to claim 17, wherein, when the ratio between the blood pressure values in the upper limb and the lower limb plotted on the same right or left side is an abnormal value, the layout unit generates the report further comprising another indicator having a length depending on the value of the ratio and a beginning point at the origin on one of the third and the fourth axis on which the blood pressure values in the lower limbs are plotted.

21. The bioinformation outputting device according to claim 19, wherein, the layout unit generates the report in which the smaller the ratio is, the longer the indicator is.

* * * * *